US006815421B1

(12) United States Patent
Tam

(10) Patent No.: US 6,815,421 B1
(45) Date of Patent: Nov. 9, 2004

(54) POLYPEPTIDES FOR USE IN AMELIORATING EFFECTS OF AGING IN MAMMALS

(75) Inventor: Cherk Shing Tam, Oakville (CA)

(73) Assignee: Osteopharm Inc., Oakville (CA)

( * ) Notice: Subject to any disclaimer, the term of this patent is extended or adjusted under 35 U.S.C. 154(b) by 0 days.

(21) Appl. No.: 10/103,132

(22) Filed: Mar. 22, 2002

Related U.S. Application Data

(60) Provisional application No. 60/277,646, filed on Mar. 22, 2001.

(51) Int. Cl.$^7$ .......................... A61K 38/00; A61K 38/18

(52) U.S. Cl. .............................. 514/12; 514/13; 514/14; 514/15; 530/300; 530/324; 530/326; 530/350; 435/7.2

(58) Field of Search .............................. 514/12, 13, 14, 514/15; 530/300, 324, 326, 350; 435/7.2

(56) References Cited

U.S. PATENT DOCUMENTS

| | | |
|---|---|---|
| 4,320,118 A | 3/1982 | White et al. |
| 4,877,864 A | 10/1989 | Wang et al. |
| 4,897,348 A | 1/1990 | Johnston et al. |
| 5,011,691 A | 4/1991 | Oppermann et al. |
| 5,024,841 A | 6/1991 | Chu et al. |
| 5,229,489 A * | 7/1993 | Kanmera et al. ........... 530/324 |
| 5,264,214 A | 11/1993 | Rhee et al. |
| 5,354,557 A | 10/1994 | Oppermann et al. |
| 5,461,034 A | 10/1995 | Rodan et al. |
| 5,470,911 A | 11/1995 | Rhee et al. |
| 5,514,775 A * | 5/1996 | Hogue-Angeletti et al. . 530/326 |
| 5,578,569 A | 11/1996 | Tam |
| 5,661,127 A | 8/1997 | Bhatnagar et al. |
| 5,786,327 A | 7/1998 | Tam |
| 5,880,094 A | 3/1999 | Tam |
| 6,004,926 A | 12/1999 | Shimizu et al. |
| 6,048,837 A | 4/2000 | Friedman et al. |
| 6,100,047 A * | 8/2000 | Wilkison et al. .............. 435/7.2 |
| 6,117,839 A * | 9/2000 | Tam ............................ 514/12 |
| 6,166,080 A | 12/2000 | Larsen et al. |
| 6,194,578 B1 | 2/2001 | Griffith et al. |
| 6,274,702 B1 | 8/2001 | Tam |
| 6,352,973 B1 | 3/2002 | Tam |

FOREIGN PATENT DOCUMENTS

| | | | |
|---|---|---|---|
| EP | 0451867 A1 | 10/1991 | |
| EP | 0499242 A1 | 8/1992 | |
| EP | 0504938 | 9/1992 | |
| GB | 2231872 | 7/1992 | |
| WO | WO90/00060 | 1/1990 | |
| WO | WO90/06321 | 6/1990 | |
| WO | WO91/11515 | 8/1991 | |
| WO | WO92/14481 | 9/1992 | |
| WO | WO94/05309 | 3/1994 | |
| WO | WO94/20615 | 9/1994 | |
| WO | WO95/28172 | 10/1995 | |
| WO | 98/26070 * | 6/1998 | .......... A61K/38/18 |

OTHER PUBLICATIONS

Online Medical Dictionary. "Aging". http://cancerweb.ncl.ac.uk/cgi–bin/omd?query=aging. Dec. 12, 1998.*

Trovato et al. Effects of age, gender and hyperparathyroidism on lean body mass in hemodialysis patients. Eur Rev Med Pharmacol Sci. Mar.–Apr. 1998;2(2):89–95.*

Tam et al., "Bone Biopsy in the Diagnosis of Primary . . . " Endoc. Calc. Metab. Excerpa Med. 427 (Abstract).

Selye, "On the Stimulation of New Bone–Formation . . . " Endocrinology 16:547–558 (1933).

Aitken et al. "Primary Hyperparathyroidism with Osteosclerosis . . . " Am. J. Med. 37: 813–820 (Nov. 1964).

Kalu et al., "Parathyroid Hormone and Experimental . . . " Lancet 1363–1366 (Jun. 1970).

Klein et al., "Prostaglandins: Simulation of Bone Resorption . . . " Endocrinology 86: 1436–14 1440 (Jun. 1970).

Connor et al., "Generalized Osteosclerosis in Primary . . . " Trans Am. Clin. Climato. Assoc. 85: 185–201 (1973).

Genant, "Osteosclerosis in Primary Hyperparathyroidism" Am. J. Med. 59: 104–113 (Jul. 1975).

Rudinger et al. Peptide Hormones. Parsons, eds., University Park Press, Baltimore, pp. 1–7, 1976.

Tam et al., "Bone Apposition Rate as an Index of . . . " Metabolism 27(2): 143–150 (Feb. 1978).

Begg et al., "Complete Covalent Structure of Human . beta.–Thromboglobulin", Structure of .beta.–Thromboglobulin, vol. 17, No. 9, 1978, pp. 1739–1744.

Schulz et al., Principles of Protein Structure, Springer–Verlag, New York, pp. 14–16, 1979.

Marks et al., "The Hematogenous Origin of Osteoclasts: Experimental . . . " Am. J. Anat 161: 1–10 (1981).

Chen, "Glucocorticoid Regulation of 1.25(OH)2–Vitamin D3 . . . " J. Bio. Chem. 257(22): 13564–13569 (Nov. .1982).

Parfitt, "The Coupling of Bone Formation to Bone . . . " Metab. Bone Dis. & Rel. Res. 4:1–6 (1982).

Tam et al., "Parathyroid Hormone Stimulates the Bone . . . " Endocrinology 110(2): 506–512 (1982).

(List continued on next page.)

Primary Examiner—Christopher R. Tate
Assistant Examiner—Maury Audet
(74) Attorney, Agent, or Firm—John C. Hunt

(57) ABSTRACT

Method of ameliorating effects of aging in an animal, the method comprising administering to the animal an effective amount of a synthetic polypeptide comprising an amino acid sequence that has 10+q amino acids, wherein, under physiological conditions, residues numbered n, n+4, n+9 are positively charged amino acids, residues numbered n+3, n+7 are negatively charged amino acids, wherein the remaining amino acids are nonpolar amino acids or uncharged polar amino acids, wherein n is an integer from 1 to 1+q and q is a whole number greater than or equal to zero. Experiments demonstrating the effect were performed with a polypeptide having the sequence Arg-Thr-Gln-Glu-His-Thr-Ala-Glu-Cys-Lys.

8 Claims, 20 Drawing Sheets

OTHER PUBLICATIONS

C.W. Castor et al., "Structural and Biological Chacteristics of Connective Tissue Activating Peptide (CTAP–III), a Major Human Platelet–3 derived Growth Factor", Proc. Natl. Acad. Sci. USA, vol. 80, Fed. 1983, pp. 765–769.

Chyun, "Stimulation of Bone Formation by Prostaglandin E2" Prostaglandins J. 27(1): 97–103 (Jan. 1984).

Canalis, "Effect of Growth Factors on Bone Cell . . . " Clin. Orthop. & Rel. Res. 246–263 (1985).

Dart et al. Transforming growth factors from a human tumor cell: characterization of transforming growth factor beta and identification of high molecular weight transforming growth factor alpha. Biochemistry, (Oct. 8, 1985) 24 (21) 5925–31.

Owen, "Lineage of Osteogenic Cells and Their . . . " Bone & Mineral Res. 3(1):1–25 (1985).

Sundelin et al, "The Primary Structure of Rabbit and Rat Prealbumin . . . " J. Biol. Chem. 260(10):6481–6487 (May 1985).

George et al., Macromolecular Sequencing and Synthesis: Selected Methods and Applications, Schlesinger, ed., Alan R. Liss Inc., New York, pp. 127–149, 1988.*

Castor et al., "Connective Tissue Activation—Biologically Active Cleavage Products of CTAP–III From Human Platelets", Biochemical and Biophysical Research Communications, vol. 163, No. 2, 1989, pp. 1071–1078.

Noda et al. In vivo stimulation of bone formation by transforming growth factor–beta. Endocrinology, (Jun. 1989) 124(6) 2991–4.

Tam, "The Pathogenesis of Metabolic Bone Disease . . . " CRC Press, Boca Raton 2: 19–31 (1989).

Bowie et al. Science 247: 1306–1310, 1990.

Walz et al., "Generation of the Neutrophil–Activating Peptide NAP–2 from Platelet Basic Protein or Connective Issue–3 Activating Peptide III Through Monocyte Proteases", Journal of Med., vol. 171, Feb. 1990, pp. 449–454.

Wells, Biochemistry 29:8509–8517, 1990.*

Wozney et al., J. Cell. Sci. Suppl. 13:149–156 (1990).

Castor et al., "Connective Tissue Activation", Arthritis & Rheumatism vol. 35, No. 7, Jul. 1992, pp. 783–793.

Roodman, "Perspectives: Interleukin–6: An Osteotropic Factor?" J. Bone & Mineral Res. 7(5): 475–478 (1992).

Ngo et al. The Protein Folding Problem and Tertiary Structure Prediction. Merz et al, eds., Birkhauser, Boston, pp. 491–495, 1994.

Vaughan et al., Identification and Characterization of the Insertion Element IS1070 from *Leuconostoc lactis* NZ6009, Elsevier Science B.V. pp. 95–100 (1995).

Navab et al., "Rat Plasma Prealbumin" J. Biol. Chem. 252:5100–5106 (Jul. 1997).

Vaughan et al., U17353, *Leuconostoc lactis* insertium sequence IS 1070:Is1070 putative transposase (tnp) gene, complete eds.

Stedman's Medical Dictionary, $27^{th}$ edition Medical Economics Company, Inc. 2000.

Abstract—WO 92/10515, Pharma Bissendorf Peptide GmbH, Derivatives of the Human Parathormone Fragment (1–37) in the Amide or Ethylamide Form as Active Substance, Jun. 25, 1992.

Abstract—WO 92/15615, Chugai Seiyaku Kabushiki Kaisha, Serum Calcium Depressing Factor, Sep. 27, 1992.

* cited by examiner

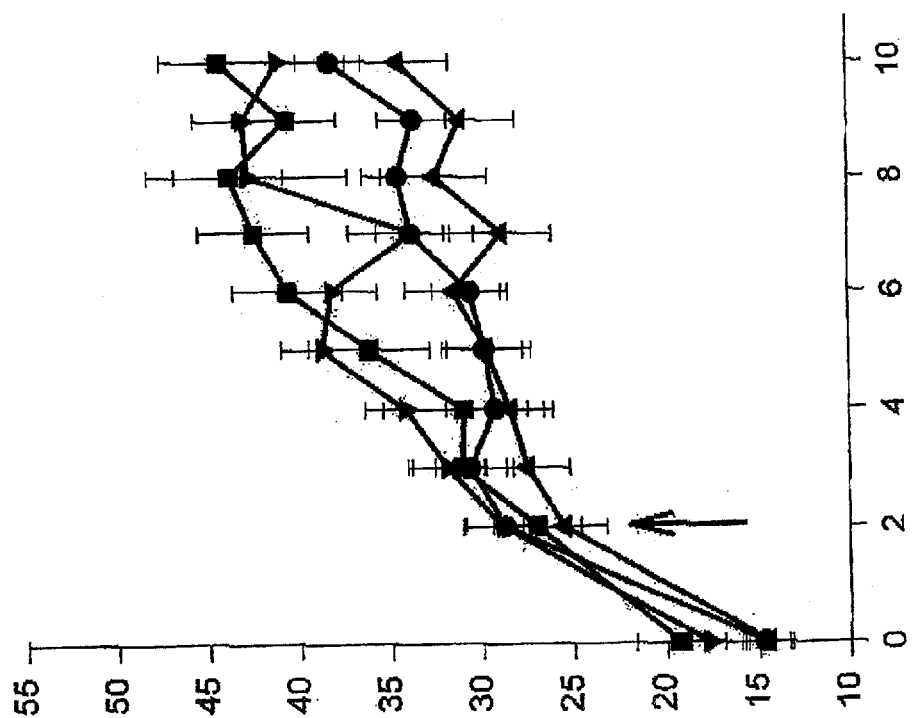

FIGURE 18

POLYPEPTIDES FOR USE IN AMELIORATING EFFECTS OF AGING IN MAMMALS

PRIOR APPLICATION

This application claims priority from U.S. provisional patent application No. 60/277,646, filed Mar. 22, 2001, the specification of which is incorporated herein in its entirety.

FIELD OF INVENTION

This invention relates to a family of polypeptides having properties which ameliorate or retard effects of aging in mammals, particularly by reducing age related increase in fat, and/or reducing age related decrease in lean body mass.

BACKGROUND OF INVENTION

Obesity, defined as an excess of body fat relative to lean body mass, is thought to be associated with important psychological and medical morbidities, the latter including cardiovascular disease, hypertension, elevated blood lipids, and Type II or non-insulin-dependent diabetes melitis (NIDDM). Despite a vast amount of research, the molecular factors regulating food intake and body weight balance are incompletely understood. Myriad approaches to reducing obesity and associated effects have been attempted over the years. There remains a persistent need for addressing these problems, but a particularly useful approach would be one that involves a reduction in the general increase in the amount of body fat relative to lean body mass that occurs with aging.

SUMMARY OF INVENTION

In one broad aspect, the present invention is a method of ameliorating effects of aging in an animal. The method includes administering to the animal an effective amount of a chemical compound that includes a synthetic polypeptide comprising an amino acid sequence that has 10+q amino acids, wherein, under physiological conditions, residues numbered n, n+4, n+9 are positively charged amino acids, residues numbered n+3, n+7 are negatively charged amino acids, wherein the remaining amino acids are nonpolar amino acids or uncharged polar amino acids, wherein n is an integer from 1 to 1+q and q is a whole number greater than or equal to zero.

When it is stated herein that an amino acid is positively charged under physiological conditions, it is meant that the side chain group of the amino acid within the polypeptide, e.g. the amino group of a lysine, would be at least 10% protonated in an aqueous solution of pH about 6.5 and ionic strength 0.1. Likewise, when it is stated herein that an amino acid is negatively charged under physiological conditions, it is meant that the side chain group of the amino acid within the polypeptide, e.g. the carboxyl group of aspartate, would be at least 10% deprotonated under such conditions.

Preferably, the animal to which the polypeptide is administered is a mammal, most preferably a human.

In one aspect, ameliorating effects of aging includes reducing an age-related increase in fat.

In another, ameliorating effects of aging includes reducing an age-related decrease in lean body mass.

In yet another, ameliorating effects of aging includes reducing age-related reduction in bone mineral content-body weight ratio of the subject.

In yet another, ameliorating effects of aging include includes reducing age-related reduction in lean body mass-body weight ratio of the mammal.

There are preferred embodiments of the polypeptide, particularly one in which any one or more of the following is true: the amino acid at position n is arginine; n+1 is threonine or alanine; n+2 is asparagine or glutamine; n+3 is glutamic acid or aspartic acid; n+4 is histitdine, n+5 is threonine or alanine; n+6 is alanine or glycine; n+7 is glutamic acid or aspartic acid; n+8 is cysteine, alanine, tyrosine or serine; and n+9 is lysine. Preferably all of these conditions are met by the polypeptide part of the chemical compound.

In particular embodiments, at least one of the following is true: the amino acid at position n is arginine; n+3 is glutamic acid or aspartic acid; n+4 is histitdine, n+7 is glutamic acid or aspartic acid; and n+9 is lysine. Again, these conditions can be met in any combination with each other.

In other embodiments, at least one of the following are true: the amino acid at position n+1 is threonine or alanine; n+2 is asparagine or glutamine; n+5 is threonine or alanine; n+6 is alanine or glycine; and n+8 is cysteine, alanine, tyrosine or serine, yet again in any combination with each other.

In other embodiments, the polypeptide includes the amino acid sequence identified as SEQ ID NO:2 or SEQ ID NO:3 wherein up to 26 amino acids of the sequence have been deleted provided that amino acids 5 to 14 of the sequence are not deleted, or a substituted variant thereof in which (i) a non-polar, aliphatic neutral amino acid has been substituted for another non-polar, aliphatic neutral amino acid, (ii) a polar aliphatic neutral amino acid has been substituted for another polar aliphatic neutral amino acid, (iii) a charged acidic amino acid has been substituted for another charged acidic amino acid, (iv) a charged basic amino acid has been substituted for another charged basic amino acid, (v) cysteine has been substituted by alanine, or (vi) a combination of substitutions (i)–(v) has been made, in which said synthetic polypeptide ameliorates effects of aging in an animal.

In other embodiments, the polypeptide includes a sequence of amino acids which is encoded by a DNA that specifically hybridizes with DNA encoding the polypeptide consisting of any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, and which polypeptide ameliorates effects of aging in a mammal or retards effects of aging in a mammal.

SEQ ID NO:2 is encoded by the nucleotide sequence designated SEQ ID NO:45, as follows:

```
GGG ATC GGA AAA CGA ACA AAT GAA CAT ACG GCA GAT TGT AAA ATT AAA
Gly Ile Gly Lys Arg Thr Asn Glu His Thr Ala Asp Cys Lys Ile Lys

CCG AAC ACC TTG CAT AAA AAA GCT GCA GAG ACT TTA ATG GTC CTT GAC
Pro Asn Thr Leu His Lys Lys Ala Ala Glu Thr Leu Met Val Leu Asp

CAA AAT GAA CCA
Gln Asn Gln Pro
```

A person skilled in the art will understand that, due to the well known degeneracy of the genetic code, that there are other coding sequences that encode SEQ ID NO:2. Further, the polypeptide fragments of the present invention are similarly encoded by corresponding portions of SEQ ID NO:45.

A DNA sequence encoding a polypeptide having SEQ ID NO:1 (unprotected version identified as SEQ ID NO:35) is identified as SEQ ID NO:54. DNA sequences encoding polypeptides have SEQ ID NOs: 2 to 9, and 11 to 20 are identified as SEQ ID NOs:45 to 53 and 55 to 63, respectively. Unprotected versions of polypeptides identified as SEQ ID NOs:1, 10 to 20 and 33 are identified as SEQ ID NOs: 35, 9, 34, 36 to 44 and 2, respectively.

In other embodiments, the polypeptide includes a sequence of amino acids selected from the following group of sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and conservatively substituted variants of each of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 and SEQ ID NO:20 which ameliorate effects of aging in a mammal.

In particularly preferred embodiments, the polypeptide is one which ameliorates effects of aging in a mammal and includes a sequence of amino acids selected from the following group of sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

In a particularly preferred embodiment, the polypeptide is one which ameliorates effects of aging in a mammal and includes SEQ ID NO:1.

Another aspect of the invention is a method of manufacturing a medicament for use in ameliorating effects of aging in a mammal. The method includes the following steps:

(a) providing a composition in dosage form, the composition containing a chemical compound of the present invention (see above);

(b) packaging the composition; and (c) providing the package with a label instructing a user to administer the composition as a medicament for use in ameliorating effects of aging in a mammal, including any or all of the age-related effects described above.

BRIEF DESCRIPTION OF DRAWINGS

FIG. 5 is a plot of body fat (g) (y-axis) vs time (month; x-axis) for ovariectomized rats over the 10-month period of the experiments: ●, tall cage, treated animals; ■, tall cage, untreated animals; ▲, low cage, treated animals; and ▼, low cage, untreated animals.

FIG. 18 shows amino acid sequences of polypepude molecules representing a family of polypeptides expected to have the properties demonstrated for the polypeptide identified as SEQ ID NO:1. The sequences below the line would be expected not to show activity. See international patent publication No. WO 0075185.

DESCRIPTION OF PREFERRED EMBODIMENTS

A polypeptide having the amino acid sequence, $Xaa_1$-Thr-Gln-Glu-His-Thr-Ala-Glu-Cys-$Xaa_{10}$, where $Xaa_1$ is N-acetyl arginine and $Xaa_{10}$ is lysinamide (SEQ ID NO:1) was subject of preliminary testing as described below.

Experimental Procedures and Conditions

Experiments were conducted using female Sprague-Dawley rats that were about 5 months old at the beginning of the experiments. The rats were obtained from Vivarium of the University of Toronto, Mississauga, Ontario, Canada.

The rats were housed in pairs in either a standard shoebox cage 15 cm in height (low cage) or a cage with 22 cm height (tall cage). Humidity was maintained at 50%; temperature 22° C.; dark/light cycle of 12 hours. The rats were fed Standard Purina Rat Chow (unlimited daily supply) and tap water ad libitum.

Ovariectomies were performed under general isofluorane anaesthesia. A 1.5 cm dorsal midline incision was made. The skin and subcutaneous tissue were separated by blunt dissection. A small incision was made on either side in the posterior abdominal muscle wall (approximately 0.5 cm) to expose the ovaries. The ovaries were removed together with the proximal ends of the Fallopian tubes after the ligation of the ovarian arteries. The wounds in the abdominal muscle wall were not stitched. The dorsal skin wound was closed by three surgical wound clips. Tamgesic (0.2 ml) was given subcutaneously for the relief of pain immediately after the operation.

Body weight measurements were made by direct weighing with an electronic balance (to 0.01 g) and by DEXA measurement, Instrument: Hologic 4500A with program for regional measurement for small animals. The animals were scanned supine under general isofluorane anaesthesia. The whole body was scanned including the whole tail. The weights for the mineral content, the fat content and the lean body mass were summed to obtain total body weight.

Non-treated (control) animals were injected subcutaneously daily with 400 μL of 20 mM sodium acetate (pH 4.5) 5 days per week. Treated animals were injected subcutaneously with 300 nmoles per kg of body weight of the test polypeptide (SEQ ID NO:1) in 400 μL of 20 mM sodium acetate (pH 4.5) daily five days per week. The treatment period was nine months. The material, chemically synthesized, was obtained from the Protein DNA Core facility of Queen's University, Kingston, Ontario, Canada. Purification, by HPLC, indicated the test compound to be at least 95% pure.

Usefulness of DEXA for the Determination of Body Composition

Figure 1:
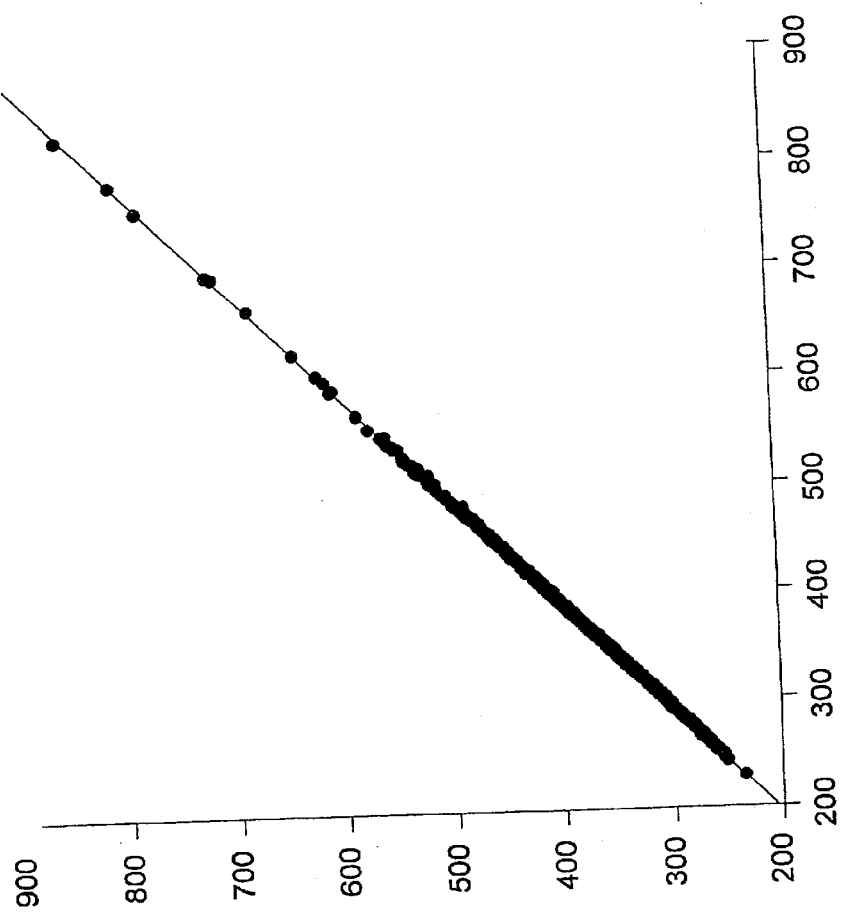
FIG. 1 is a plot of bodyweight (g) as measured by Hologic DEXA (y-axis) vs bodyweight measured directly using an electronic balance. A total of 667 paired measurements are plotted. $b(0)=0.789$; $b(1)=1.022$ and $r^2=0.9998$.

DEXA measurements were evaluated as an indication of body composition. Through the attenuation of X-ray energy DEXA measurements provide an indication of the mass of various body tissues. In the Hologic DEXA instrument, the program measures the mass of bone tissue, fat and lean body mass (largely muscle mass). The sum of these measured masses represents total body mass. If this proposition is correct, then the total body mass measured by DEXA and measured directly by balance will be the same. Over the course of these experiments, 677 paired measurements of the body weight were made using the two methods. The results obtained (FIG. 1) indicate that there is a close relationship between the DEXA measurements and the measurements. It was thus concluded that body composition could be assessed using DEXA measurements.

Experimental Protocol

Eight groups of rats were treated as follows:

| | | |
|---|---|---|
| Tall cages: | Intact, untreated | 8 rats |
| | Intact, treated | 8 rats |
| | OVX, untreated | 9 rats |
| | OVX, treated | 9 rats |
| Low cages: | Intact, untreated | 8 rats |
| | Intact, treated | 8 rats |
| | OVX, untreated | 9 mts |
| | OVX, treated | 10 rats |

Ovariectomies were performed at the age of 5 months. The ovariectomized animals were allowed to lose bone for two months following ovariectomy before the treatment began. A baseline measurement was made immediately prior to operation. Another pretreatment baseline measurement was made at the beginning of treatment, i.e. two months after ovariectomization. Measurements were made approximately monthly thereafter. At the end of the experiments, all animals were sacrificed by carbon dioxide narcosis.

Procedures were carried out according to the following schedule:

| Day | Procedure |
|---|---|
| 1, 2 | Ovariectomy, baseline DEXA and weighing |
| 63 | Pretreatment base line DEXA and weighing |
| 95 | DEXA and weighing |
| 126 | DEXA and weighing |
| 160 | DEXA and weighing |
| 191 | DEXA and weighing |
| 223 | DEXA and weighing |
| 255 | DEXA and weighing |
| 286 | DEXA and weighing |
| 318 | DEXA and weighing |
| 349 | Animal sacrifice |

Results and Discussion

Results obtained were analyzed to determine the correlation between controlled parameter and observed measurements, as described below.

Effect of Cage Height, Ovariectomization and Polypeptide on Total Body Weight

Figure 2:
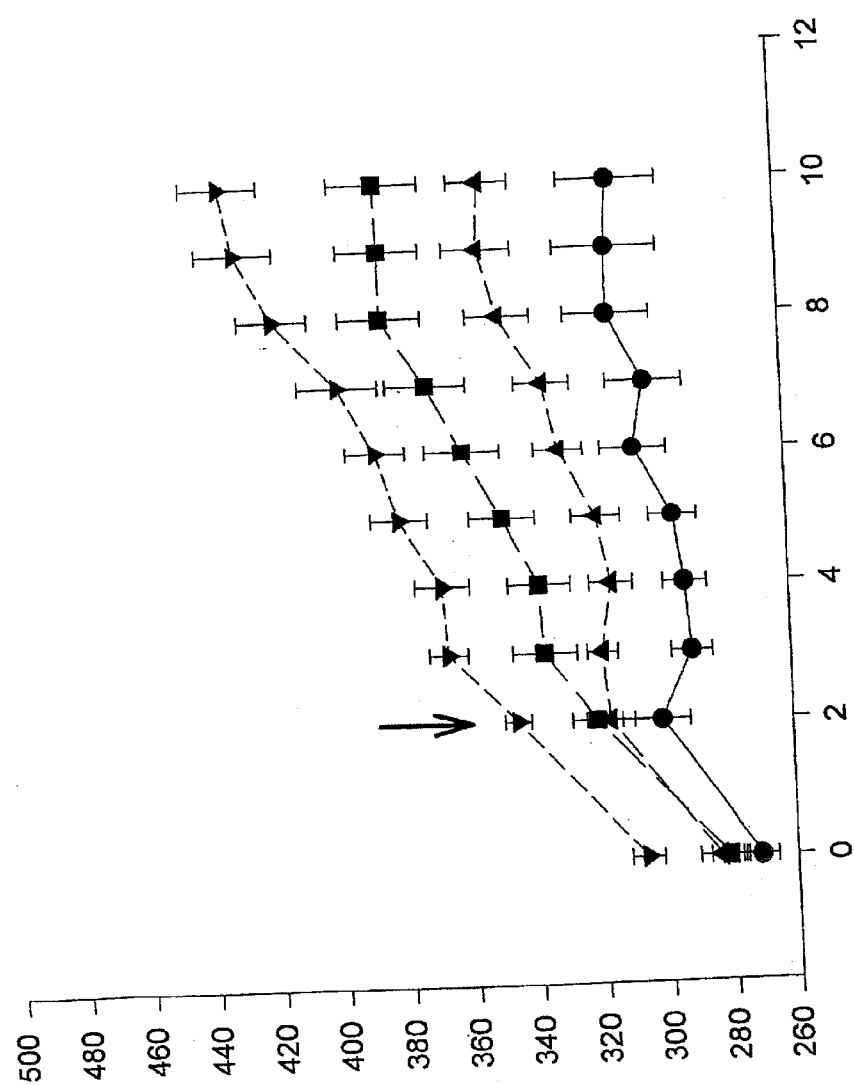
FIG. 2 is a plot of average total bodyweight (g; y-axis) vs time (months; x-axis) for intact rats (non-ovariectomized) over the 10-month period of the experiments: ●, tall cage, treated animals; ■, tall cage, untreated animals; ▲, low cage, treated animals; and ▼, low cage, untreated animals. The error bars represent standard error, for this and all other figures. Treatment began after two months (downward arrow; 63 days) and, as the rats were about 5 months of age at t=0, the animals aged from about 5 to about 15 months over the 10-month period of the experiments. Each point represents the average of the results obtained with eight rats.

All animal groups experienced a gain in overall body weight over the 10-month experimental period from 5 to 15 months of age, as shown in FIG. 2. The gain was most pronounced from 5 to 7 months of age, i.e., the first two months of the experimental period. After that, the observed weight gain slowed and, more or less, leveled off by the age of 13 months.

Effect of Ovariectomy on Body Weight

Figure 3:
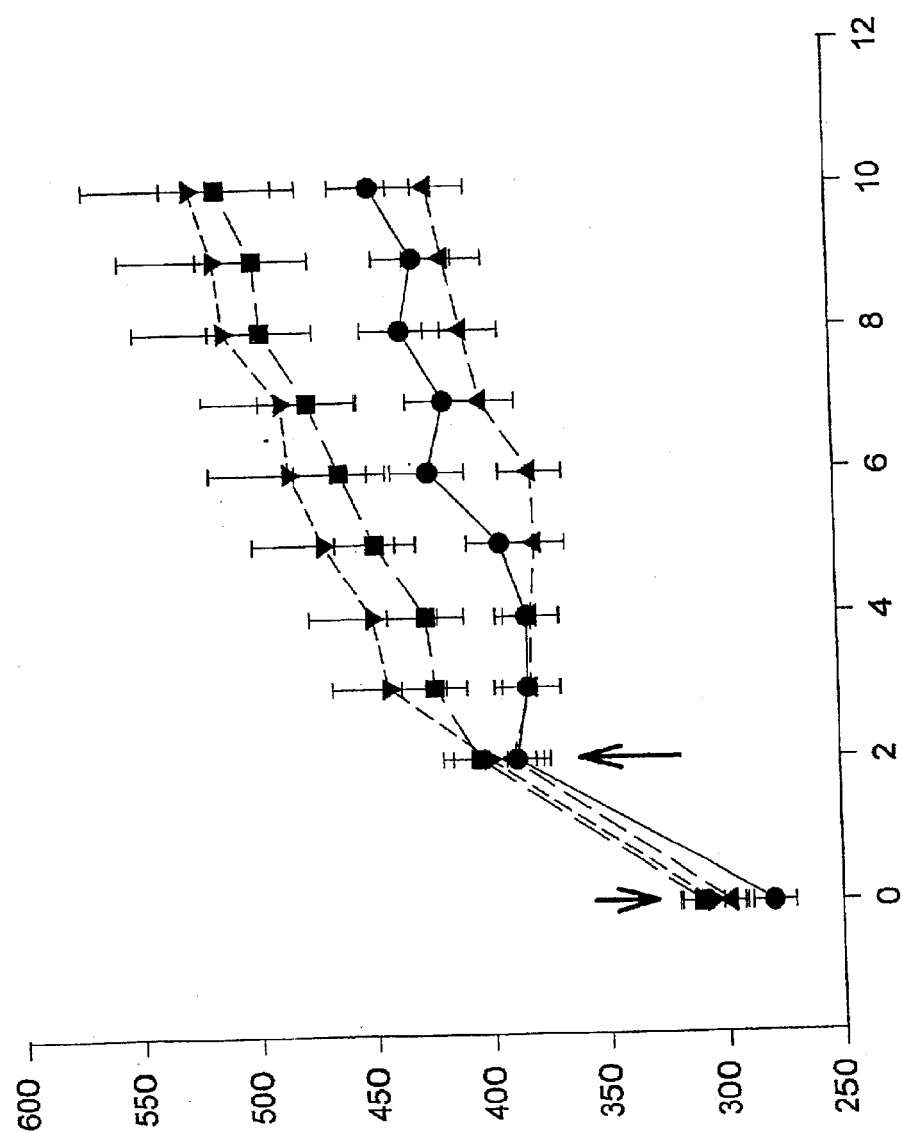
FIG. 3 is a plot of average total bodyweight (g; y-axis) vs time (months; x-axis) for ovariectomized rats (downward arrow) as follows: ●, tall cage, treated animals; ■, tall cage, untreated animals; ▲, low cage, treated animals; and ▼, low cage, untreated animals. As the rats were about 7 months of when treatment started (upward arrow), the animals aged from about 7 to about 15 months over the 8-month treatment period. Each point represents the average of the results obtained with nine rats, except in the case of treated rats in low cages, where there were ten rats.

Ovariectomized rats gained weight more rapidly than intact rats, particularly during the first two months following the operation. The gain during this time period was about 100 g or more, as shown in FIGS. 2 and 3.

Effect of Cage Height on Body Weight

For intact rats subject to otherwise similar conditions, those housed in the taller cages experienced lower overall weight gain than those housed in the shorter cages, as shown in FIG. 2. In the case of ovariectomized rats, cage height had a relatively small effect, as shown in FIG. 3.

Effect of Polypeptide Treatment on Total Body Weight Gain

Intact rats treated with the polypeptide (SEQ ID NO:1) experienced a lower age-related gain in total body weight, as shown in FIG. 2. The relative decrease was not largely affected by a change in cage height, a condition which permits greater physical activity on the part of the rats. As described below, the observed reduction in overall weight gain was largely at the expense of a gain in weight due to fat.

Ovariectomized rats treated with the polypeptide experienced a relative decrease in overall weight gain, although the effect seemed to be smaller than that observed for intact rats, as shown in FIG. 3.

Effect of Polypeptide Treatment on Body Fat Content

Figure 4:
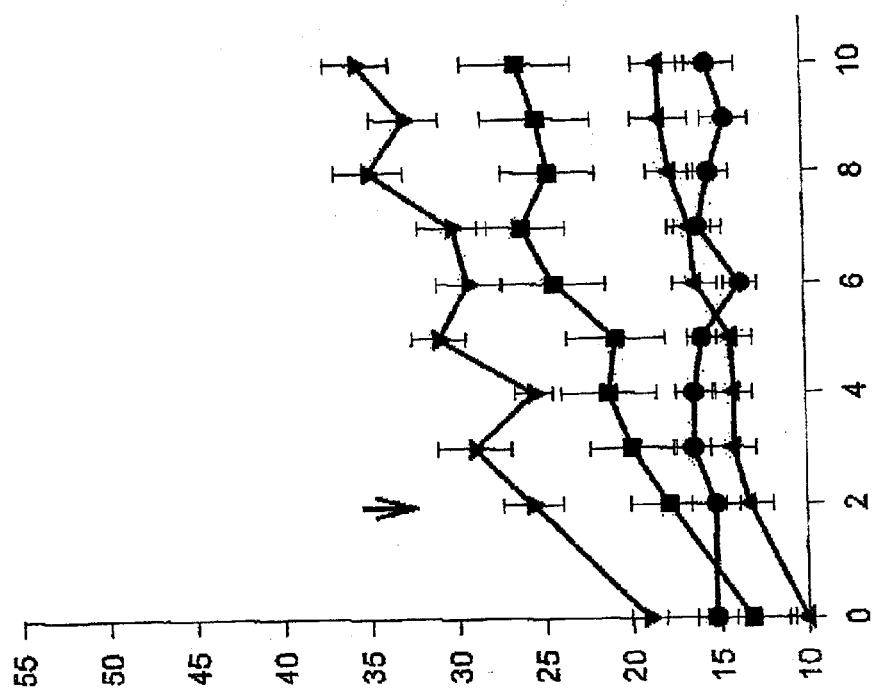
FIG. 4 is a plot of body fat (g) (y-axis) vs time (month; x-axis) for intact rats over the 10-month period of the experiments: ●, tall cage, treated animals; ■, tall cage, untreated animals; ▲, low cage, treated animals; and ▼, low cage, untreated animals.
Figure 6A:
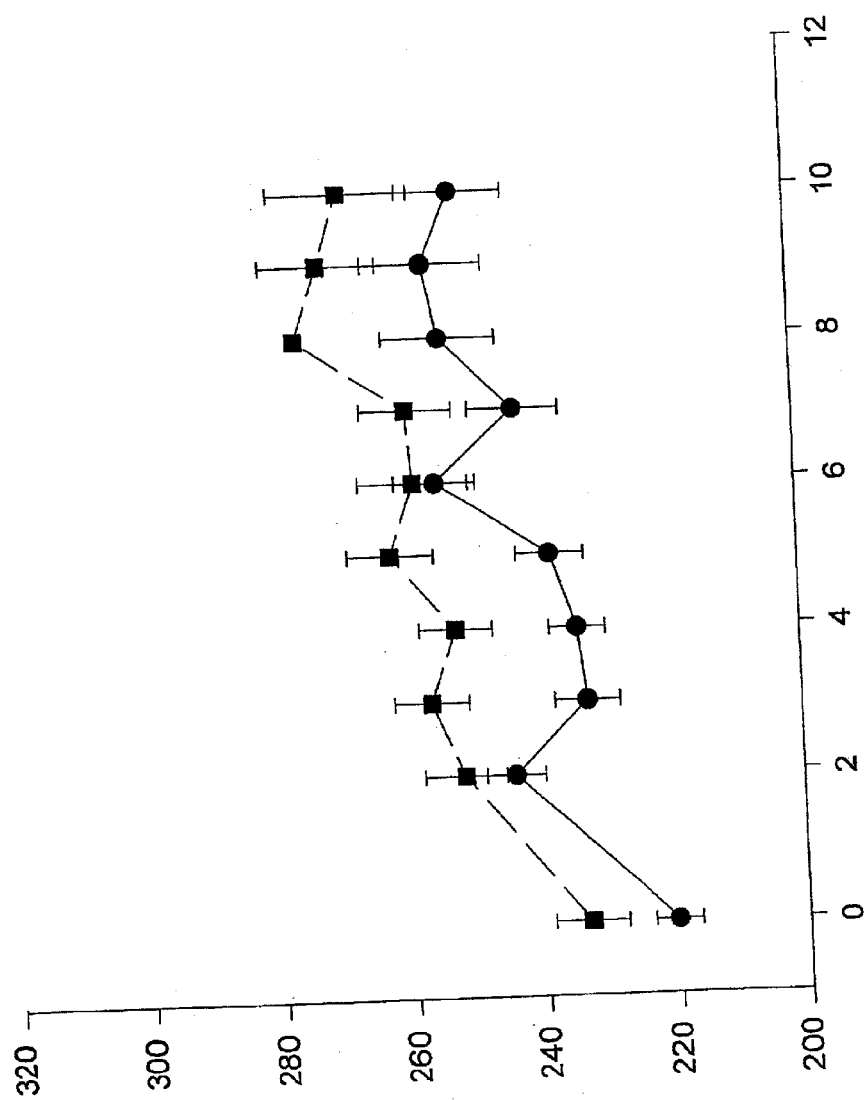
FIG. 6A is a plot of average lean body mass (g; y-axis) vs time (months; x-axis) for intact rats housed in tall cages over the 10-month experimental period: ●, treated; and ■, untreated.
Figure 6B:
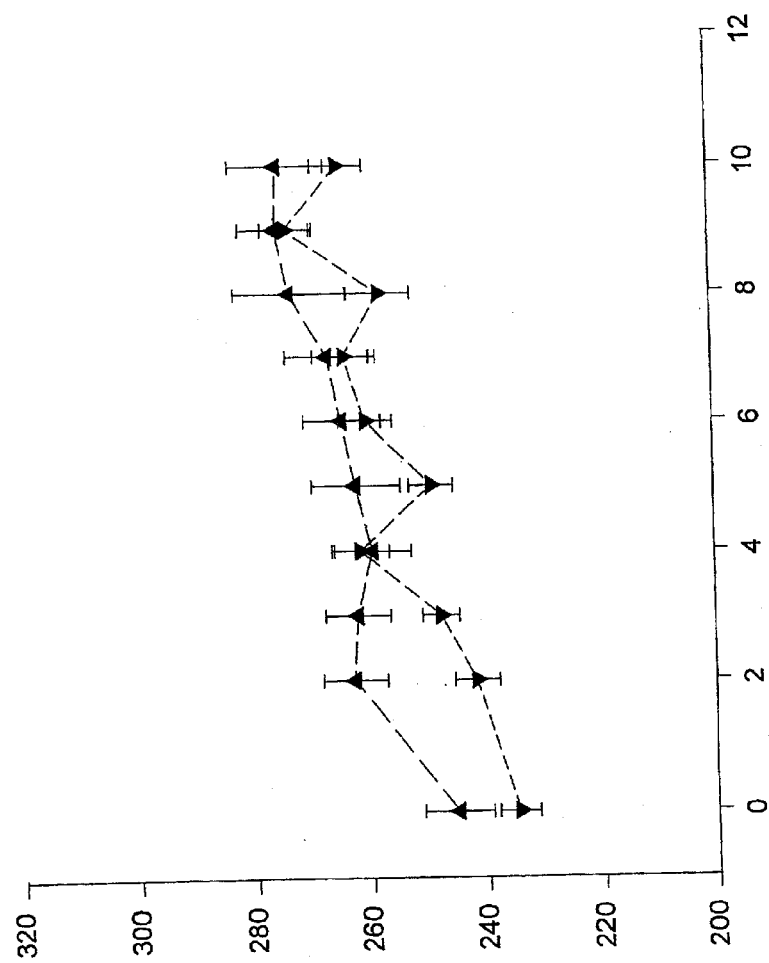
FIG. 6B is a plot of average lean body mass (g; y-axis) vs time (months; x-axis) for intact rats housed in low cages over the 10-month experimental period: ▼, treated; and ▲, untreated.
Figure 7A:
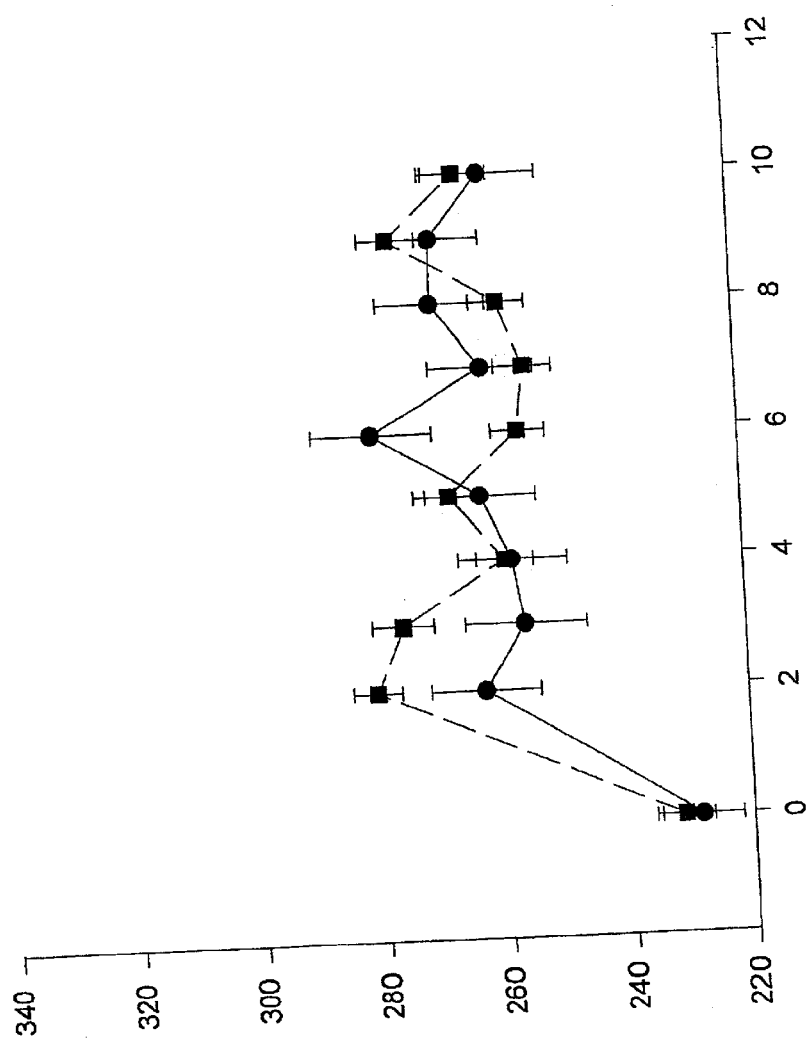
FIG. 7A is a plot of average lean body mass (g; y-axis) vs time (months; x-axis) for ovariectomized rats housed in tall cages over the 10-month experimental period: ●, treated; and ■, untreated.
Figure 7B:
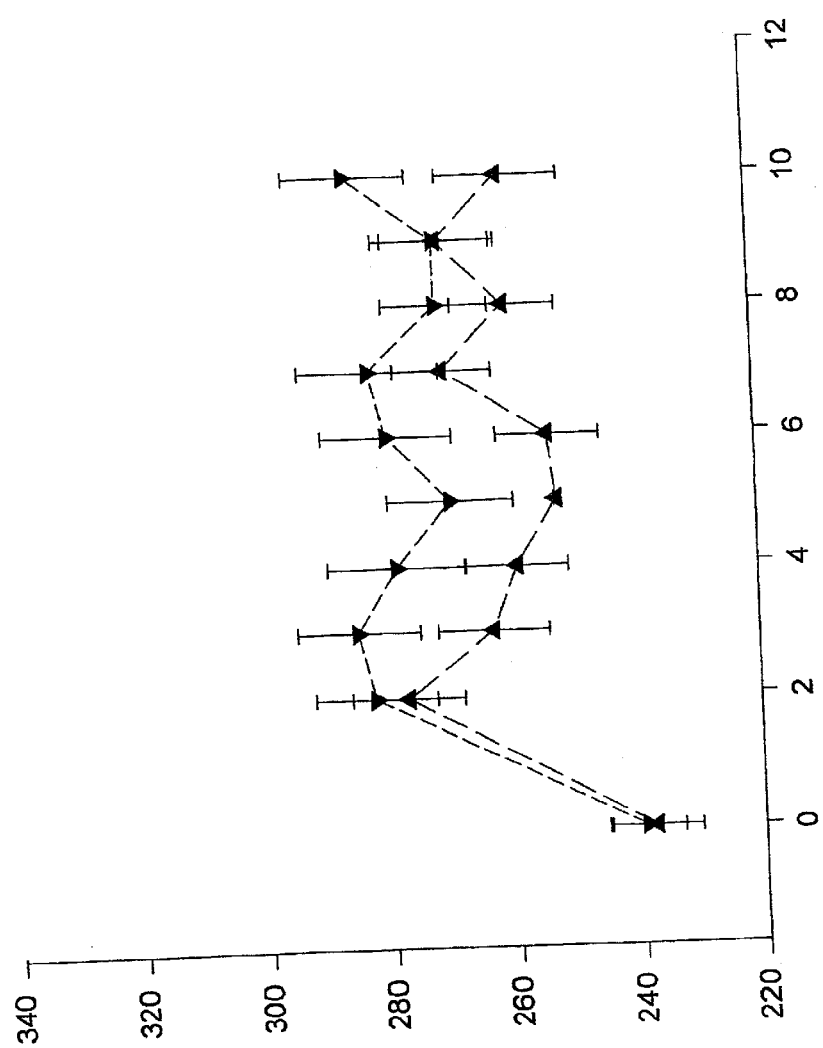
FIG. 7B is a plot of average lean body mass (g; y-axis) vs time (months; x-axis) for ovariectomized rats housed in low cages over the 10-month experimental period: ▼, treated; and ▲, untreated.

Body fat content, expressed grams was determined and plotted as function of time. See FIGS. 4 and 5.

In the case of intact rats not treated with the polypeptide, an increase in fat content was observed as the rats aged and the increase was relatively independent of the height of cages in which the rats were housed, although a small reduction in fat gain was observed for rats housed in tall cages. See FIGS. 4 and 5.

For intact rats treated with the polypeptide, the increase in fat content was reduced in comparison to the untreated (control) rats, and the reduction appeared to be greatest for rats housed in tall cages.

During the first two months following ovariectomization, there was relatively rapid gain in body fat, as can be seen in FIG. 5. During the treatment period (from seven to fifteen months of age of the rats), the change in fat content observed in the untreated ovariectomized rats was similar to that observed in the intact rats. Ovariectomized rats treated with the polypeptide experienced a significantly smaller increase in body fat content when housed in taller cages, and less so when housed in low cages, as shown in FIG. 5.

Effect of Polypeptide Treatment on Lean Body Mass

A relatively small change in lean body mass was observed for all groups of rats over the 10-month experimental period, as shown in FIGS. 6A to 7B.

Effect of Polypeptide Treatment on Bone Mineral Content

An age-related gain in bone mineral content was observed for all groups of rats over the 10-month experimental period. The BMC gain was very pronounced for the first two months, leveling by about eighth to ninth months of the experiment (13 to 14 months of age). See FIGS. 8 and 9.

Cage height appeared to have a relatively small influence on bone mineral content.

Ovariectomized rats appeared to experience a greater increase bone mineral content with age than the intact rats. This appears to be in contrast with that observed in human beings, in which total body mineral content has been observed to decrease after menopause.

Figure 8:
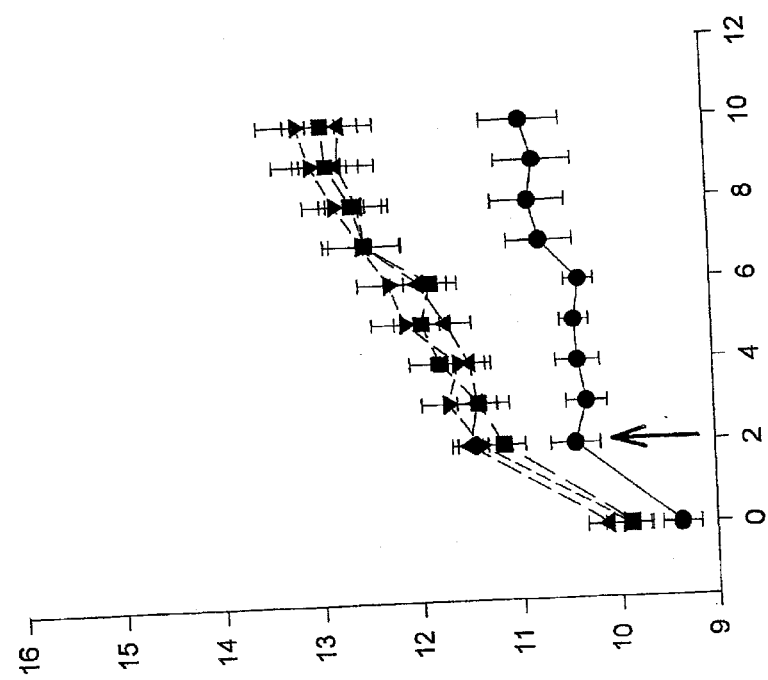
FIG. 8 is a plot of average bone mineral content (g; y-axis) vs time (months; x-axis) for intact rats over the 10-month experimental period: ●, tall cage, treated animals; ■, tall cage, untreated animals; ▼, low cage, treated animals; and ▲, low cage, untreated animals.
Figure 9:
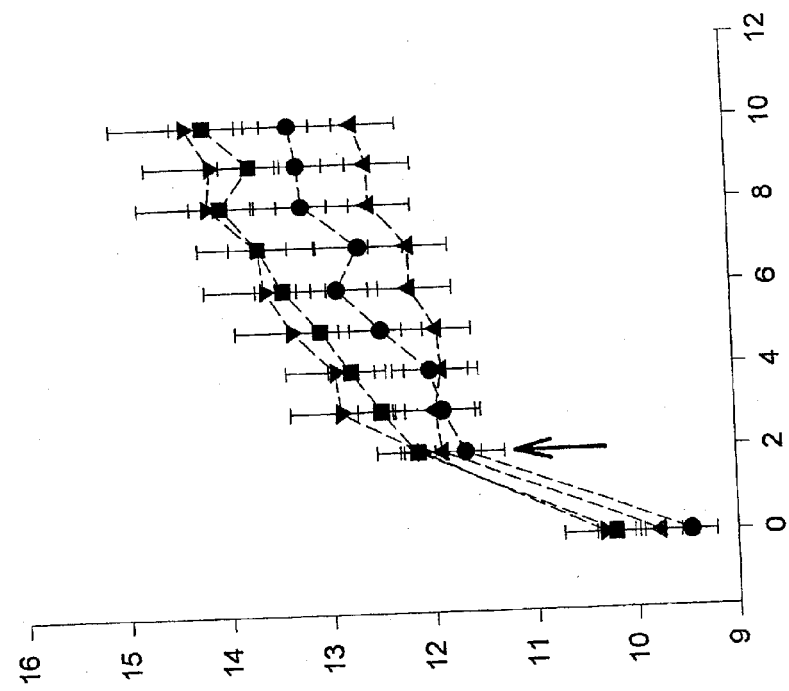
FIG. 9 is a plot of average bone mineral content (g; y-axis) vs time (months; x-axis) for ovariectomized rats over the 10-month experimental period: ●, tall cage, treated animals; ■, tall cage, untreated animals; ▼, low cage, treated animals; and ▲, low cage, untreated animals.

An attenuation of the increase in bone mineral content was observed for rats treated with the polypeptide, for both intact and ovariectomized rats, as shown in FIGS. 8 and 9.

Bone Mineral Content and Body Weight

The percent change in the ratio of BMC/BW as a function of time was plotted. See FIGS. 10 to 13.

Figure 10:
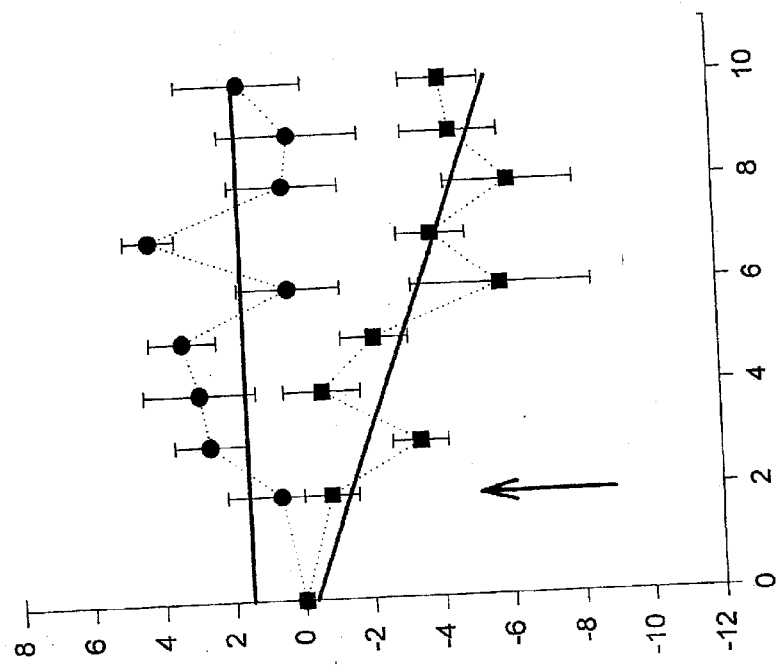
FIG. 10 is a plot of percent change in average BMC/BW (y-axis) vs time (months; x-axis) for intact rats housed in tall cages over the 10-month experimental period: ●, treated; and ■, untreated.
Figure 11:
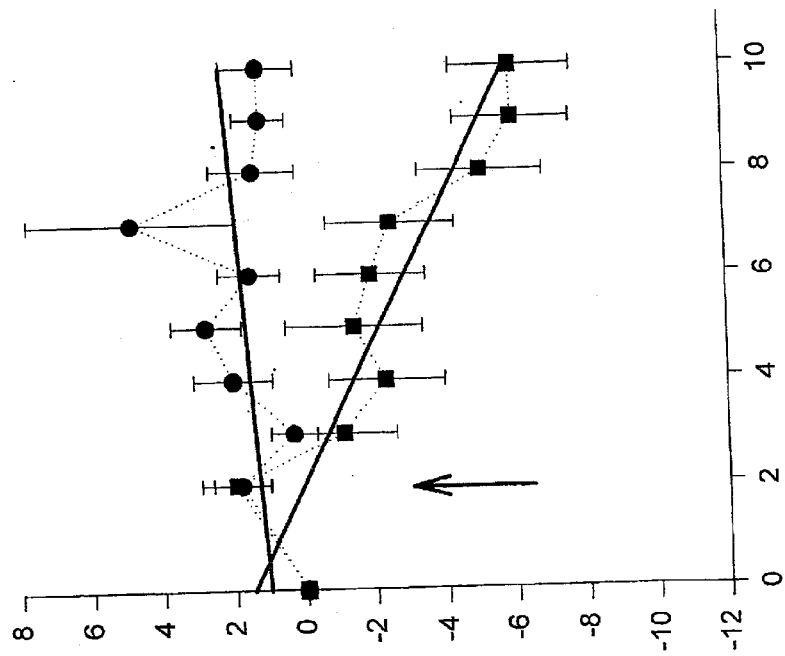
FIG. 11 is a plot of percent change in average BMC/BW (y-axis) vs time (months; x-axis) for intact rats housed in low cages over the 10-month experimental period: ●, treated; and ■, untreated.

As can be seen in FIGS. 10 and 11, there was a decrease in the BMC/BW ratio with time for intact rats, and the decrease was similar for rats housed in both types of cages. The BMC/BW ratio changed much less for those rats that were treated with the polypeptide.

Figure 12:
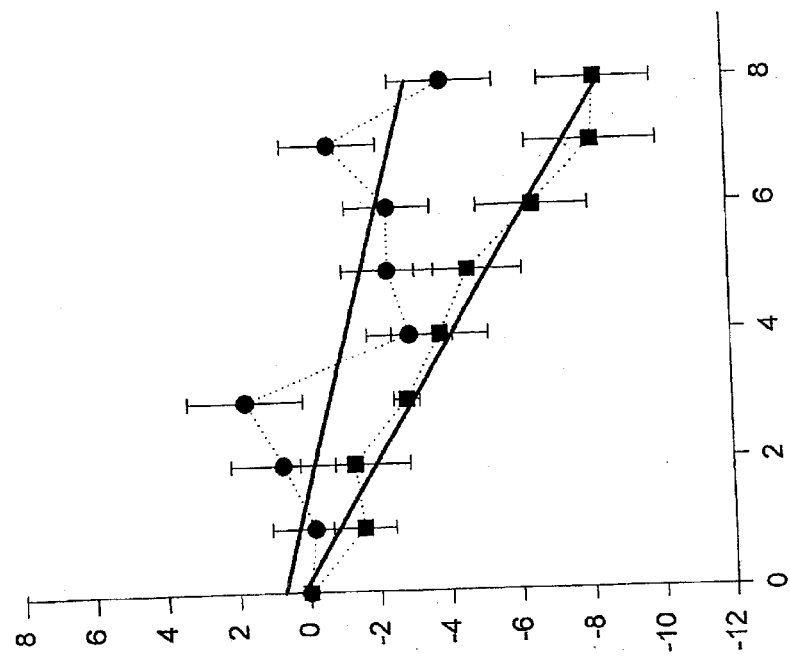
FIG. 12 is a plot of percent change in average BMC/BW (y-axis) vs time (months; x-axis) for ovariectomized rats housed in tall cages over the 8-month treatment period: ●, treated; and ■, untreated.
Figure 13:
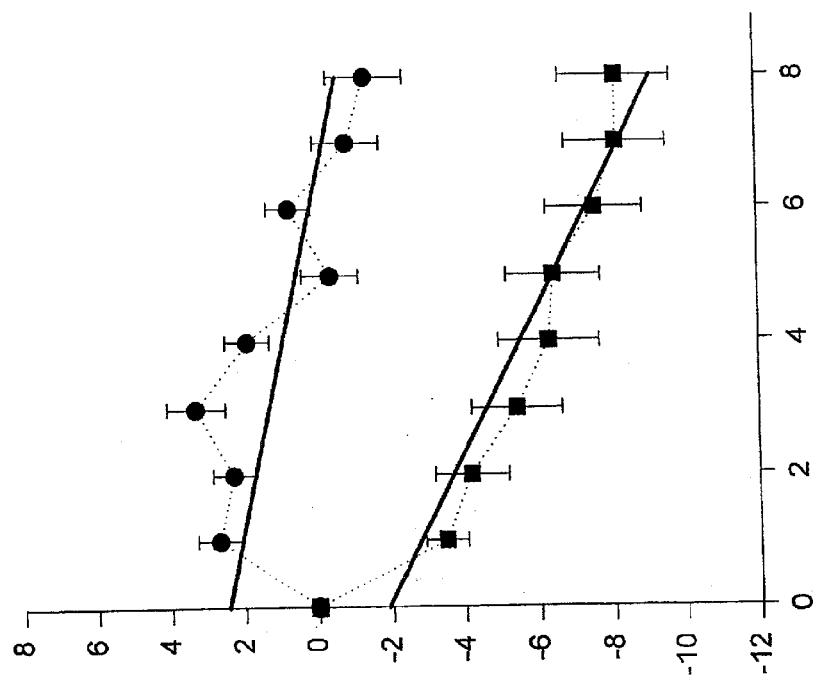
FIG. 13 is a plot of percent change in average BMC/BW (y-axis) vs time (months; x-axis) for ovariectomized rats housed in low cages over the 8-month treatment period: ●, treated; and ■, untreated.

As can be seen in FIGS. 12 and 13, there was a similar decrease in the BMC/BW ratio with time for ovariectomized rats, compared to the intact rats, and again the decrease was similar for rats housed in both types of cages. In the case of ovariectomized rats, however, the attenuating effect of polypeptide treatment appeared to be less pronounced.

Polypeptide treatment thus appears to ameliorate the effect of aging on the BMC/BW ratio. Insofar as it would be expected that an increase in the BMC/BW ratio would provide a benefit, by increasing the relative load-bearing capacity of the bone than would be otherwise, this would appear to be a salutary effect of polypeptide treatment.

Lean Body Mass and Body Weight

The percent change in the ratio of LBM/BW as a function of time was plotted. See FIGS. 14 to 17.

Figure 14:
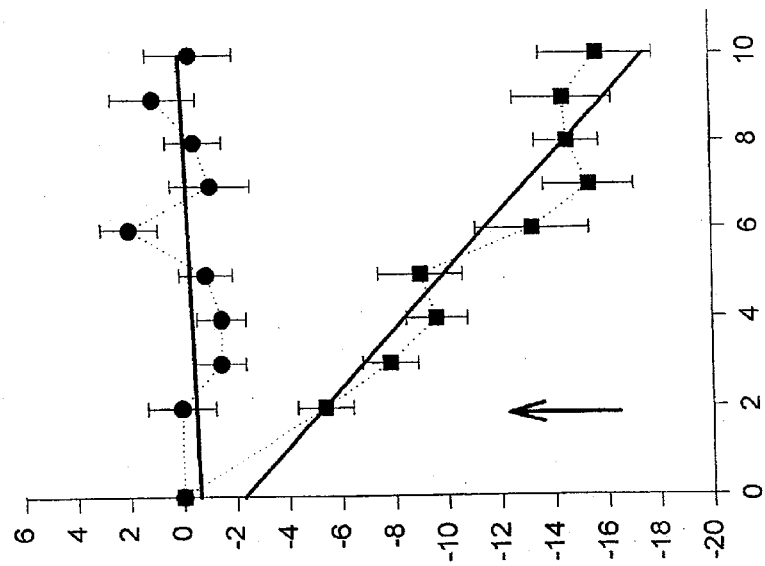
FIG. 14 is a plot of percent change in average LBM/BW (y-axis) vs time (months; x-axis) for intact rats housed in tall cages over the 10-month experimental period: ●, treated; and ■, untreated.
Figure 15:
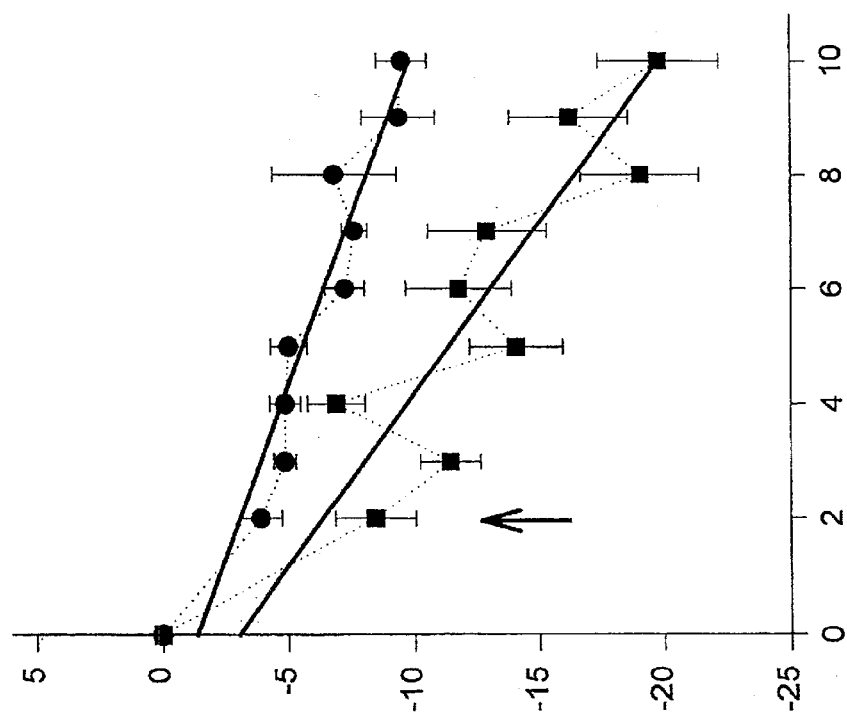
FIG. 15 is a plot of percent change in average LBM/BW (y-axis) vs time (months; x-axis) for intact rats housed in low cages over the 10-month experimental period: ●, treated; and ■, untreated.

As can be seen in FIGS. 14 and 15, there was a decrease in the LBM/BW ratio with time for intact rats, and the decrease was similar for rats housed in both types of cages. The LBM/BW ratio changed much less for those rats that were treated with the polypeptide.

Figure 16:
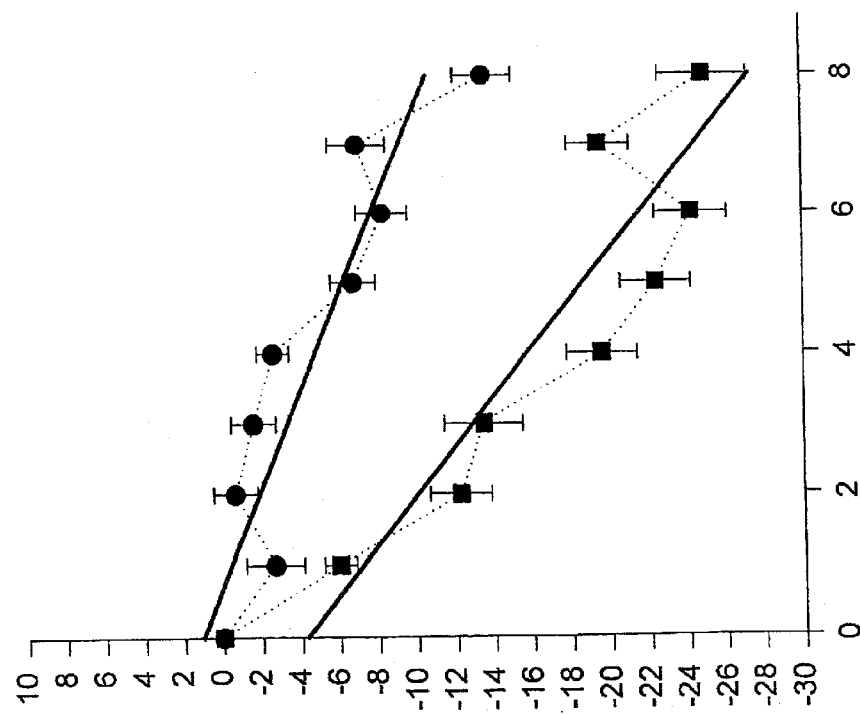
FIG. 16 is a plot of percent change in average LBM/BW (y-axis) vs time (months; x-axis) for ovariectomized rats housed in tall cages over the 8-month treatment period: ●, treated; and ■, untreated.
Figure 17:
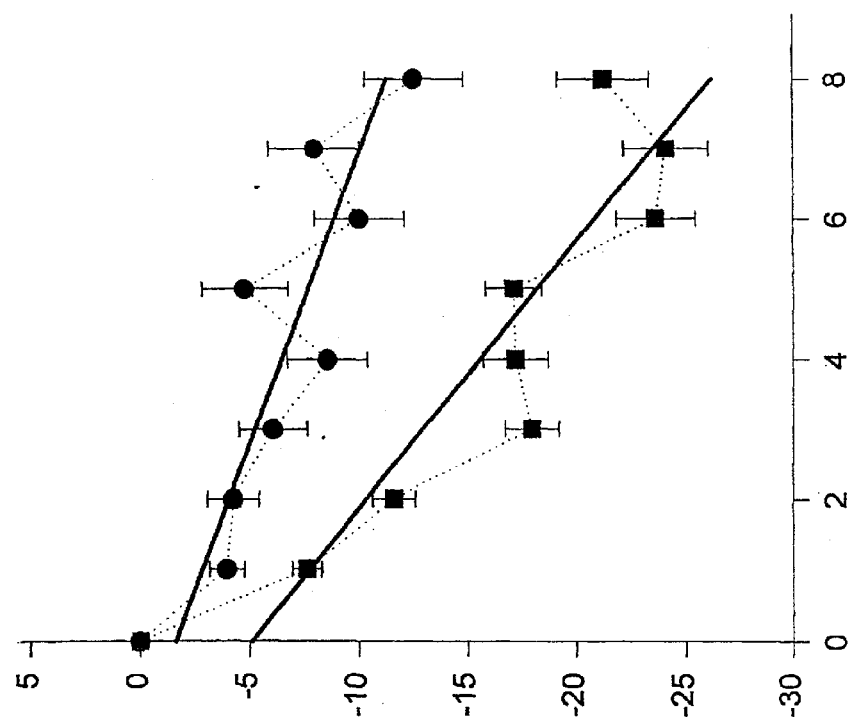
FIG. 17 is a plot of percent change in average LBM/BW (y-axis) vs time (months; x-axis) for ovariectomized rats housed in low cages over the 8-month treatment period: ●, treated; and ■, untreated.

As can be seen in FIGS. 16 and 17, there was a greater decrease in the LBM/BW ratio with time for ovariectomized rats, compared to intact rats. Again, however, the decrease was similar for rats housed in both types of cages. The attenuating effect of polypeptide treatment on the change in LBM/BW ratio over time appeared to be greater for intact rats than it was for ovariectomized rats.

The major component of lean body mass is muscle. Polypeptide treatment appears to ameliorate the effect of aging on the LBM/BW ratio. Insofar as it would be expected that an increase in the LBM/BW ratio would provide a benefit, by increasing the body muscle content than would be otherwise the case, this would appear to be a salutary effect of polypeptide treatment.

| List of Abbreviations | |
|---|---|
| BMC | Bone mineral content |
| BW | Body weight |
| DEXA | Dual-energy X-ray absorptiometry |
| LBM | Lean body mass |
| OVX | Ovariectomized rat |

As indicated above, the test polypeptide (SEQ ID NO:1) is a 10-mer, protected at both ends and having the following amino acid sequence:

Xaa Thr Gln Glu His Thr Ala Glu Cys Xaa wherein Xaa in the first position is N-acetyl arginine and Xaa in the tenth position is lysinamide.

Also part of this invention is use of any of the family of polypeptides set out as follows in FIG. 18, and identified as SEQ ID NOs:2 to 20.

A "variant" of a specific polypeptide disclosed herein refers to an amino acid sequence that is altered with respect to the specifically disclosed sequence by one or more amino acids. The variant may have "conservative" changes, wherein a substituted amino acid has similar structural or chemical properties, e.g., replacement of leucine with isoleucine. Typical such substitutions are among Ala, Val, Leu and lie; among Ser and Thr; among the acidic residues Asp and Glu; among Asn and Gln; and among the basic residues Lys and Arg; or aromatic residues Phe and Tyr. A variant of a polypeptide may be a naturally occurring such as an allelic variant, or it may be a variant that is not known to occur naturally. Non-naturally occurring variants of polypeptides may be made by mutagenesis techniques, by direct synthesis; and by other recombinant methods known to skilled artisans. Similar minor variations may also include amino acid deletions or insertions, or both. Further guidance in determining which amino acid residues may be substituted, inserted, or deleted without abolishing biological or immunological activity may be found using computer programs well known in the art, for example, DNASTAR software.

Included as part of this invention are use of polypeptides that contain such conservatively substituted variants of any of SEQ ID NOs:1 to 20. Of course the cysteine residue occupying the position numbered thirteen in SEQ ID NO:2 can be replaced by any of alanine, tyrosine, and serine, as activity of the polypeptide is conserved when such a substitution is made.

Figure 18:
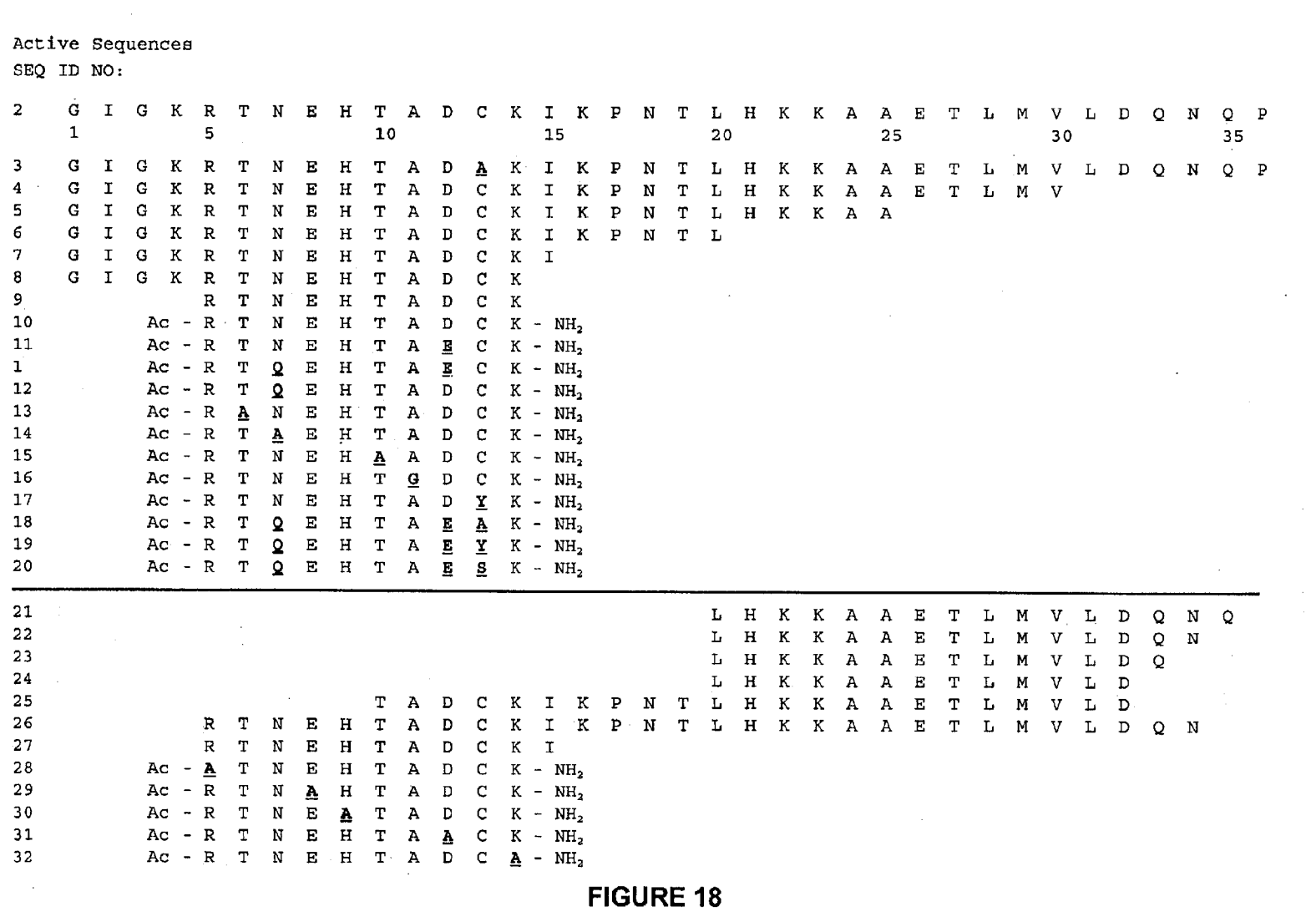

Also shown in the lower portion of FIG. 18 is a series of polypeptides each of which were found in the past to lack bone stimulatory activity and so would be expected to lack the utility of this invention. Such information provides guidance to a skilled person when designing variant polypeptides of those explicitly shown as SEQ ID NOs:1 to 20. This is particularly useful for obtaining active fragments of the largest polypeptide sequences, SEQ ID NOs:2 and 3.

A more complete description of the activity of the sequences shown in FIG. 18 is given in: international patent application No. PCT/CA00/00673 published under WO 0075185 Dec. 14, 2000; international patent application No. PCT/CA97/00967 published under WO9826070 Jun. 18, 1998; international patent application No. PCT/CA00100673 published under WO 0075185 Dec. 14, 2000; international patent application No. PCT/CA96/00401 published under WO 009640909 Dec. 19, 1996; and international patent application No. PCT/CA94/00144 published under WO 9420615 on Sep. 15, 1994. The specification of each of these documents is incorporated herein by reference.

In addition to polypeptides consisting only of naturally-occurring amino acids, the present invention includes peptidomimetics. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) Adv. Drug Res. 15: 29; Veber and Freidinger (1985) TINS p.392; and Evans et al. (1987) J. Med. Chem 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —$CH_2NH$—, —$CH_2S$—, —$CH_2CH_2$—, —$CH=CH$— (cis and trans), —$COCH_2$—, —$CH(OH)CH_2$—, and —$CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., Int J Pept Prot Res (1979) 14:177–185 (—$CH_2NH$—, —$CH_2CH_2$—); Spatola, A. F. et al., Life Sci (1986) 38:1243–1249 (—$CH_2S$—); Hann, M. M., J Chem Soc Perkin Trans I (1982) 307–314 (—$CH=CH$—, cis and trans); Almquist, R. G. et al., J Med Chem (1980) 23:1392–1398 (—$COCH_2$—); Jennings-White, C. et al., Tetrahedron Lett (1982) 23:2533 (—$COCH_2$—); Szelke, M. et al., European Appln. EP 45665 (1982) CA: 97:39405 (1982) (—$CH(OH)CH_2$—); Holladay, M. W. et al., Tetrahedron Lett (1983) 24:4401–4404 (—$C(OH)CH_2$—); and Hruby, V. J., Life Sci (1982) 31:189–199 (—$CH_2S$—); each of which is incorporated herein by reference. A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labelling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., receptor molecules) to which the peptidomimetic binds to produce the therapeutic effect. Derivitization (e.g., labelling) of peptidomimetics should not substantially interfere with the desired biological or pharmacological activity of the peptidomimetic.

As discussed above, a polypeptide (or analogue thereof) of the present invention finds utility in the treatment of obesity as it relates to age related increase in body fat, or in modulation of body weight as it relates to reducing age related decrease in lean body mass.

The present invention includes utilities that extend to methods for measuring the presence and extent of a polypeptide of the invention in biological extracts (or samples) taken from a subject being treated for obesity or other condition for which the polypeptide has effect. In this way the level of the polypeptide being administered can be monitored in an individual, be it by a doctor, clinician, or even the subject, provided with a suitable diagnostic kit. A kit can include an antibody to the particular polypeptide or analogue thereof being administered. Generation of an antibody to a polypeptide having the amino acid sequence identified as SEQ ID NO:2 has previously been described, for example, in international patent application No. PCT/CA94/00144 published under WO 94/20615 on Sep. 15, 1994. The antibody can thus be linked to or conjugated with any of several well known reporter systems set up to indicate positively binding of the polypeptide to the antibody. Well known reporter systems include radioimmuno assays (RIAs) or immunoradiometric assays (IRMAs). Alternatively, an enzyme-linked immunosorbent assay (ELISA) would have in common with RIAs and IRMAs a relatively high degree of sensitivity, but would generally not rely upon the use of radioisotopes. A visually detectable substance may be produced or at least one detectable in a spectrophotometer. An assay relying upon fluroescence of a substance bound by the enzyme being assayed could be used. It will be appreciated that there are a number of reporter systems which may be used, according to the present invention, to detect the presence of a particular polypeptide. With standardized sample collection and treatment, polypeptide presence below or above a threshold amount in blood serum, urine, or other sample can be determined. This in turn can be used in determining dosage levels, administration frequency, and other aspects of the treatment regimen.

Also included in the invention are the use of the polypeptides of the invention in competitive assays to identify or quantify molecules having receptor binding characteristics corresponding to those of said polypeptides. The polypeptides may be labelled, optionally with a radioisotope. A competitive assay can identify both antagonists and agonists of the relevant receptor.

The polypeptides and analogues of the invention have significant potential in the treatment of age related increase in fat, and/or reducing age related decrease in lean body mass. Preferably, a therapeutically effective amount of such an agent is administered in a pharmaceutically acceptable carrier, diluent, or excipient. The dosages and dosage regimen in which an agent is administered will vary according to the dosage form, mode of administration, the condition being treated and particulars of the patient being treated. Accordingly, optimal therapeutic concentrations will be best determined at the time and place through routine testing.

The agent can be delivered by intravenous, intraarterial, intraperitoneal, intramuscular, or subcutaneous routes of administration. Alternatively, the polypeptide, properly formulated, can be administered by nasal or oral administration. A constant supply of the agent can be ensured by providing a therapeutically effective dose (i.e., a dose effective to induce metabolic changes in a subject) at the necessary intervals, e.g., daily, every 12 hours, etc. These parameters will depend on the severity of the condition being treated, other actions, such as diet modification, that are implemented, the weight, age, and sex of the subject, and other criteria, which can be readily determined according to standard good medical practice by those of skill in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Such preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The phrase "pharmaceutically acceptable" refers to molecular entities and compositions that are physiologically tolerable and do not typically produce an allergic or similarly untoward reaction, such as gastric upset, dizziness and the like, when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the agent is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical carriers are described in Martin, Remington's Pharmaceutical Sciences, 18th Ed., Mack Publishing Co., Easton, Pa. (1990).

The compounds according to the invention can also be administered orally in solid dosage forms, which are described generally in Martin, Chapter 89, 1990. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for therapeutics is given by Marshall, in Modern Pharmaceutics, Chapter 10, Banker and Rhodes ed., (1979). In general, the formulation will include the polypeptide or analogue thereof of choice, and inert ingredients which allow for protection against the stomach environment, and release of the biologically active material in the intestine.

Also contemplated are oral dosage forms of the derivatized agents of the invention. The agent may be chemically modified so that oral delivery of the derivative is efficacious. Generally, the chemical modification contemplated is the attachment of at least one moiety to the peptide molecule itself, where said moiety permits (a) inhibition of amidolysis; and (b) uptake into the blood stream from the stomach or intestine. Also desired is the increase in overall stability of the polypeptide increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski et al., "Soluble Polymer-Enzyme Adducts", in Enzymes as Drugs, pp.

367–383, Holcenberg and Roberts, eds., Wiley-Interscience, New York, N.Y., (1981); Newmark et al., J. Appl. Biochem., 4:185–189 (1982). Other polymers that could be used are poly-1,3-dioxolane and poly-1,3,6-tioxocane. Preferred for pharmaceutical usage, as indicated above, are polyethylene glycol moieties.

For the agent (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the polypeptide or by release of the biologically active material beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder, for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colourants and flavouring agents may all be included. For example, the polypeptide (or analogue) may be formulated (such as by liposome or microsphere encapsulation) and then further contained within an edible product, such as a refrigerated beverage containing colorants and flavoring agents.

One can dilute or increase the volume of the therapeutic with an inert material. These diluents could include carbohydrates, especially mannitol, .alpha.-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to: stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, and Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the polypeptide (or analogue) are for instance the fatty acids oleic acid, linoleic acid and linolenic acid.

Controlled release formulation may be desirable. The agent could be incorporated into an inert matrix which permits release by either diffusion or leaching mechanisms i.e., gums. Slowly degenerating matrices may also be incorporated into the formulation. Another form of a controlled release of this therapeutic is by a method based on the Oros therapeutic system (Alza Corp.), i.e. the drug is enclosed in a semipermeable membrane which allows water to enter and push the drug out through a single small opening due to osmotic effects. Some enteric coatings also have a delayed release effect.

Other coatings may be used for the formulation. These include a variety of sugars which could be applied in a coating pan. The agent could also be given in a film-coated tablet; the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Also contemplated herein is pulmonary delivery of the polypeptide (or analogue thereof). The active agent is delivered to the lungs of a mammal while inhaling and traverses across the lung epithelial lining to the blood-stream. Other reports of this include Adjei et al., Pharmaceutical Research, 7(6):565–569 (1990); Adjei et al., International Journal of Pharmaceutics, 63:135–144 (1990) (leuprolide acetate); Braquet et al., Journal of Cardiovascular Pharmacology, 13(suppl. 5):143–146 (1989) (endothelin-1); Hubbard et al., Annals of Internal Medicine, 3(3):206–212 (1989) (.alpha.1-antitrypsin); Smith et al., J. Clin. Invest., 84:1145–1146 (1989) (.alpha.1-proteinase); Oswein et al., "Aerosolization of Proteins", Proceedings of Symposium on Respiratory Drug Delivery II, Keystone, Colo., (March 1990) (recombinant human growth hormone); Debs et al., J. Immunol., 140:3482–3488 (1988) (interferon-γ and TNF-γ) and Platz et al., U.S. Pat. No. 5,284,656 (granulocyte colony stimulating factor). Contemplated for use in the practice of this invention are a wide range of mechanical devices designed for pulmonary delivery of therapeutic products, including but not limited to nebulizers, metered-dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered-dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of polypeptide (or analogue). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified polypeptide may also be prepared in different formulations depending on the type of chemical modification or the type of device employed.

Formulations suitable for use with a nebulizer, either jet or ultrasonic, will typically comprise the active agent dissolved in water at a concentration of about 0.1 to 25 mg of biologically active polypeptide per ml of solution. The formulation may also include a buffer and a simple sugar (e.g., for peptide stabilization and regulation of osmotic pressure). The nebulizer formulation may also contain a surfactant, to reduce or prevent surface induced aggregation of the peptide caused by atomization of the solution in forming the aerosol.

Formulations for use with a metered-dose inhaler device will generally comprise a finely divided powder containing the protein (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing protein (or derivative) and may also include a bulking agent, such as lactose, sorbitol, sucrose, or mannitol in amounts which facilitate dispersal of the powder from the device, e.g., 50 to 90% by weight of the formulation. The polypeptide (or analogue) should most advantageously be prepared in particulate form with an average particle size of less than 10 microns, most preferably 0.5 to 5 microns, for most effective delivery to the distal lung.

Nasal delivery of the polypeptide protein (or analogue) is also contemplated. Nasal delivery allows the passage of the active agent to the blood stream directly after administering the therapeutic product to the nose, without the necessity for deposition of the product in the lung. Formulations for nasal delivery include those with dextran or cyclodextran.

In yet another aspect of the present invention, methods of treatment and manufacture of a medicament are provided for treatment the of conditions of age related increase in fat, and/or reducing age related decrease in lean body mass. Of course, insofar as the invention is useful in treating such conditions, the invention can be said to be a prophylactic treatment. Also, since the administration is not necessarily as a medicament, but could be as part of a food, the invention extends to methods of manufacture of a food for use in reducing age related increase in fat, and/or reducing age related decrease in lean body mass.

For a polypeptide (or analogue) of the present invention, as further studies are conducted, information will emerge regarding appropriate dosage levels for treatment of various conditions in various patients, and the ordinary skilled worker, considering the therapeutic context, age and general health of the recipient, will be able to ascertain the proper dosage. Generally, for injection or infusion, dosage will be between 0.01 micrograms of biologically active protein/kg body weight, (calculating the mass of the protein alone, without chemical modification), and 10 mg/kg (based on the same). The dosing schedule may vary, depending on the circulation half-life of the agent used, whether the polypeptide is delivered by bolus dose or continuous infusion, and the formulation used.

The phrase "therapeutically effective amount" is used herein to mean an amount sufficient to obtain the desired effect, according to the condition being treated.

Where a particular polypeptide or nucleic acid molecule is said to have a specific percent identity or conservation to a reference polypeptide or nucleic acid molecule, the percent identity or conservation can be determined by the algorithm of Myers and Miller, CABIOS (1989), which is embodied in the ALIGN program (version 2.0), or its equivalent, using a gap length penalty of 12 and a gap penalty of 4 where such parameters are required. All other parameters are set to their default positions. Access to ALIGN is readily available. See, e.g., http://www2.igh.cnrs.fr/bin/align-guess.cgi on the internet.

Comparison of the sequence to the data bases can be performed using BLAST (Altschcul, S. F. et al., J. Mol. Biol. 215:403–410 (1990)).

Parameters for polypeptide sequence comparison include the following: (1) Algorithm: Needleman and Wunsch, J. Mol Biol. 48: 443–453 (1970); (2) Comparison matrix: BLOSSUM62 from Hentikoff and Hentikoff, Proc. Natl. Acad. Sci. USA. 89:10915–10919 (1992); (3) Gap Penalty: 12; and (4) Gap Length Penalty: 4. A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: (1) Algorithm: Needleman and Wunsch, J. Mol Biol. 48:443–453 (1970); (2) Comparison matrix: matches=+10, mismatch=0; (3) Gap Penalty: 50; and (4) Gap Length Penalty: 3. Available as: The "gap" program from Genetics Computer Group, Madison Wis. These are the default parameters for nucleic acid comparisons.

All references referred to herein are incorporated herein in there entirety.

What is claimed is:

1. A method of reducing obesity in a mammal in need thereof, the method comprising administering to the mammal an effective amount of a synthetic polypeptide having (i) the amino acid sequence identified as SEQ ID NO:35, wherein one or the other or both of the terminal amino acids of the polypeptide is protected, or (ii) the amino acid sequence identified as SEQ ID NO:1.

2. The method of claim 1, wherein the polypeptide is the amino acid sequence identified as SEQ ID NO:1.

3. The method of claim 1, wherein the mammal is a human.

4. The method of claim 3, wherein the polypeptide is the amino acid sequence identified as SEQ ID NO:1.

5. A method of manufacturing a medicament for use in reducing obesity in a mammal, the method comprising:

(a) providing a composition in dosage form, which comprises a synthetic polypeptide having (i) the amino acid sequence identified as SEQ ID NO:35, wherein one or the other or both of the terminal amino acids of the polypeptide is protected, or (ii) the amino acid sequence identified as SEQ ID NO:1;

(b) packaging the composition; and (c) providing the package with a label instructing a user to administer the composition as a medicament for use in reducing obesity in a mammal.

6. The method of claim 5, wherein the polypeptide is the amino acid sequence identified as SEQ ID NO:1.

7. The method of claim 6, wherein the mammal is a human.

8. The method of claim 5, wherein the mammal is a human.

* * * * *

SEQUENCE LISTING

```
<160> NUMBER OF SEQ ID NOS: 63

<210> SEQ ID NO 1
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 1

Xaa Thr Gln Glu His Thr Ala Glu Cys Xaa
1               5                   10

<210> SEQ ID NO 2
<211> LENGTH: 36
<212> TYPE: PRT
<213> ORGANISM: Homo sapiens

<400> SEQUENCE: 2

Gly Ile Gly Lys Arg Thr Asn Glu His Thr Ala Asp Cys Lys Ile Lys
1               5                   10                  15

Pro Asn Thr Leu His Lys Lys Ala Ala Glu Thr Leu Met Val Leu Asp
            20                  25                  30

Gln Asn Gln Pro
        35

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 3

Gly Ile Gly Lys Arg Thr Asn Glu His Thr Ala Asp Ala Lys Ile Lys
1               5                   10                  15

Pro Asn Thr Leu His Lys Lys Ala Ala Glu Thr Leu Met Val Leu Asp
            20                  25                  30

Gln Asn Gln Pro
        35

<210> SEQ ID NO 4
<211> LENGTH: 30
<212> TYPE: PRT
<213> ORGANISM: Homo sapiens
```

-continued

```
<400> SEQUENCE: 4

Gly Ile Gly Lys Arg Thr Asn Glu His Thr Ala Asp Cys Lys Ile Lys
  1               5                  10                  15

Pro Asn Thr Leu His Lys Lys Ala Ala Glu Thr Leu Met Val
             20                  25                  30

<210> SEQ ID NO 5
<211> LENGTH: 25
<212> TYPE: PRT
<213> ORGANISM: Homo sapiens

<400> SEQUENCE: 5

Gly Ile Gly Lys Arg Thr Asn Glu His Thr Ala Asp Cys Lys Ile Lys
  1               5                  10                  15

Pro Asn Thr Leu His Lys Lys Ala Ala
             20                  25

<210> SEQ ID NO 6
<211> LENGTH: 20
<212> TYPE: PRT
<213> ORGANISM: Homo sapiens

<400> SEQUENCE: 6

Gly Ile Gly Lys Arg Thr Asn Glu His Thr Ala Asp Cys Lys Ile Lys
  1               5                  10                  15

Pro Asn Thr Leu
             20

<210> SEQ ID NO 7
<211> LENGTH: 15
<212> TYPE: PRT
<213> ORGANISM: Homo sapiens

<400> SEQUENCE: 7

Gly Ile Gly Lys Arg Thr Asn Glu His Thr Ala Asp Cys Lys Ile
  1               5                  10                  15

<210> SEQ ID NO 8
<211> LENGTH: 14
<212> TYPE: PRT
<213> ORGANISM: Homo sapiens

<400> SEQUENCE: 8

Gly Ile Gly Lys Arg Thr Asn Glu His Thr Ala Asp Cys Lys
  1               5                  10

<210> SEQ ID NO 9
<211> LENGTH: 10
<212> TYPE: PRT
<213> ORGANISM: Homo sapiens

<400> SEQUENCE: 9

Arg Thr Asn Glu His Thr Ala Asp Cys Lys
  1               5                  10

<210> SEQ ID NO 10
<211> LENGTH: 10
<212> TYPE: PRT
<213> ORGANISM: Homo sapiens
<220> FEATURE:
<221> NAME/KEY: MOD_RES
<222> LOCATION: (1)...(1)
<223> OTHER INFORMATION: Xaa is N-acetyl arginine
<220> FEATURE:
```

```
<221> NAME/KEY: MOD_RES
<222> LOCATION: (10)...(10)
<223> OTHER INFORMATION: Xaa is lysinamide

<400> SEQUENCE: 10

Xaa Thr Asn Glu His Thr Ala Asp Cys Xaa
1               5                   10

<210> SEQ ID NO 11
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 11

Xaa Thr Asn Glu His Thr Ala Glu Cys Xaa
1               5                   10

<210> SEQ ID NO 12
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 12

Xaa Thr Gln Glu His Thr Ala Asp Cys Xaa
1               5                   10

<210> SEQ ID NO 13
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 13

Xaa Ala Asn Glu His Thr Ala Asp Cys Xaa
1               5                   10

<210> SEQ ID NO 14
<211> LENGTH: 10
<212> TYPE: PRT
```

```
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 14

Xaa Thr Ala Glu His Thr Ala Asp Cys Xaa
 1               5                  10

<210> SEQ ID NO 15
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 15

Xaa Thr Asn Glu His Ala Ala Asp Cys Xaa
 1               5                  10

<210> SEQ ID NO 16
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 16

Xaa Thr Asn Glu His Thr Gly Asp Cys Xaa
 1               5                  10

<210> SEQ ID NO 17
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide
```

```
<400> SEQUENCE: 17

Xaa Thr Asn Glu His Thr Ala Asp Tyr Xaa
 1               5                  10

<210> SEQ ID NO 18
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 18

Xaa Thr Gln Glu His Thr Ala Glu Ala Xaa
 1               5                  10

<210> SEQ ID NO 19
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 19

Xaa Thr Gln Glu His Thr Ala Glu Tyr Xaa
 1               5                  10

<210> SEQ ID NO 20
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 20

Xaa Thr Gln Glu His Thr Ala Glu Ser Xaa
 1               5                  10

<210> SEQ ID NO 21
<211> LENGTH: 16
<212> TYPE: PRT
<213> ORGANISM: Homo sapiens

<400> SEQUENCE: 21
```

-continued

Leu His Lys Lys Ala Ala Glu Thr Leu Met Val Leu Asp Gln Asn Gln
1               5                   10                  15

<210> SEQ ID NO 22
<211> LENGTH: 15
<212> TYPE: PRT
<213> ORGANISM: Homo sapiens

<400> SEQUENCE: 22

Leu His Lys Lys Ala Ala Glu Thr Leu Met Val Leu Asp Gln Asn
1               5                   10                  15

<210> SEQ ID NO 23
<211> LENGTH: 14
<212> TYPE: PRT
<213> ORGANISM: Homo sapiens

<400> SEQUENCE: 23

Leu His Lys Lys Ala Ala Glu Thr Leu Met Val Leu Asp Gln
1               5                   10

<210> SEQ ID NO 24
<211> LENGTH: 13
<212> TYPE: PRT
<213> ORGANISM: Homo sapiens

<400> SEQUENCE: 24

Leu His Lys Lys Ala Ala Glu Thr Leu Met Val Leu Asp
1               5                   10

<210> SEQ ID NO 25
<211> LENGTH: 23
<212> TYPE: PRT
<213> ORGANISM: Homo sapiens

<400> SEQUENCE: 25

Thr Ala Asp Cys Lys Ile Lys Pro Asn Thr Leu His Lys Lys Ala Ala
1               5                   10                  15

Glu Thr Leu Met Val Leu Asp
            20

<210> SEQ ID NO 26
<211> LENGTH: 30
<212> TYPE: PRT
<213> ORGANISM: Homo sapiens

<400> SEQUENCE: 26

Arg Thr Asn Glu His Thr Ala Asp Cys Lys Ile Lys Pro Asn Thr Leu
1               5                   10                  15

His Lys Lys Ala Ala Glu Thr Leu Met Val Leu Asp Gln Asn
            20                  25                  30

<210> SEQ ID NO 27
<211> LENGTH: 11
<212> TYPE: PRT
<213> ORGANISM: Homo sapiens

<400> SEQUENCE: 27

Arg Thr Asn Glu His Thr Ala Asp Cys Lys Ile
1               5                   10

<210> SEQ ID NO 28
<211> LENGTH: 10
<212> TYPE: PRT

```
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl alanine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 28

Xaa Thr Asn Glu His Thr Ala Asp Cys Xaa
 1               5                  10

<210> SEQ ID NO 29
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 29

Xaa Thr Asn Ala His Thr Ala Asp Cys Xaa
 1               5                  10

<210> SEQ ID NO 30
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide

<400> SEQUENCE: 30

Xaa Thr Asn Glu Ala Thr Ala Asp Cys Xaa
 1               5                  10

<210> SEQ ID NO 31
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is lysinamide
<220> FEATURE:
<223> OTHER INFORMATION: Description of Artificial Sequence: Chemically
      synthesized polypeptide
```

```
<400> SEQUENCE: 31

Xaa Thr Asn Glu His Thr Ala Ala Cys Xaa
 1               5                  10

<210> SEQ ID NO 32
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Xaa is N-acetyl arginine
<220> FEATURE:
<221> NAME/KEY: MOD_RES
<222> LOCATION: (10)...(10)
<223> OTHER INFORMATION: Xaa is alaninamide
<220> FEATURE:
<223> OTHER INFORMATION: Description of Artificial Sequence: Chemically
      synthesized polypeptide

<400> SEQUENCE: 32

Xaa Thr Asn Glu His Thr Ala Asp Cys Xaa
 1               5                  10

<210> SEQ ID NO 33
<211> LENGTH: 36
<212> TYPE: PRT
<213> ORGANISM: Homo sapiens
<220> FEATURE:
<221> NAME/KEY: MOD_RES
<222> LOCATION: (1)...(1)
<223> OTHER INFORMATION: Xaa is N-acetyl glycine

<400> SEQUENCE: 33

Xaa Ile Gly Lys Arg Thr Asn Glu His Thr Ala Asp Cys Lys Ile Lys
 1               5                  10                  15

Pro Asn Thr Leu His Lys Lys Ala Ala Glu Thr Leu Met Val Leu Asp
            20                  25                  30

Gln Asn Gln Pro
        35

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 34

Arg Thr Asn Glu His Thr Ala Glu Cys Lys
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 35

Arg Thr Gln Glu His Thr Ala Glu Cys Lys
 1               5                  10

<210> SEQ ID NO 36
<211> LENGTH: 10
```

```
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 36

Arg Thr Gln Glu His Thr Ala Asp Cys Lys
  1               5                  10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 37

Arg Ala Asn Glu His Thr Ala Asp Cys Lys
  1               5                  10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 38

Arg Thr Ala Glu His Thr Ala Asp Cys Lys
  1               5                  10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 39

Arg Thr Asn Glu His Ala Ala Asp Cys Lys
  1               5                  10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 40

Arg Thr Asn Glu His Thr Gly Asp Cys Lys
  1               5                  10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 41

Arg Thr Asn Glu His Thr Ala Asp Tyr Lys
```

-continued

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 42

Arg Thr Gln Glu His Thr Ala Glu Ala Lys
  1               5                  10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 43

Arg Thr Gln Glu His Thr Ala Glu Tyr Lys
  1               5                  10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Chemically
      synthesized polypeptide

<400> SEQUENCE: 44

Arg Thr Gln Glu His Thr Ala Glu Ser Lys
  1               5                  10

<210> SEQ ID NO 45
<211> LENGTH: 108
<212> TYPE: DNA
<213> ORGANISM: Homo sapiens
<220> FEATURE:
<221> NAME/KEY: CDS
<222> LOCATION: (1)...(108)

<400> SEQUENCE: 45 ggg atc gga aaa cga aca aat gaa cat acg gca gat tgt aaa att aaa         48
Gly Ile Gly Lys Arg Thr Asn Glu His Thr Ala Asp Cys Lys Ile Lys
  1               5                  10                  15 ccg aac acc ttg cat aaa aaa gct gca gag act tta atg gtc ctt gac         96
Pro Asn Thr Leu His Lys Lys Ala Ala Glu Thr Leu Met Val Leu Asp
             20                  25                  30 caa aat gaa cca                                                        108
Gln Asn Glu Pro
         35

<210> SEQ ID NO 46
<211> LENGTH: 108
<212> TYPE: DNA
<213> ORGANISM: Homo sapiens
<220> FEATURE:
<221> NAME/KEY: CDS
<222> LOCATION: (1)...(108)

<400> SEQUENCE: 46 ggg atc gga aaa cga aca aat gaa cat acg gca gat gca aaa att aaa         48

```
Gly Ile Gly Lys Arg Thr Asn Glu His Thr Ala Asp Ala Lys Ile Lys
1               5                   10                  15 ccg aac acc ttg cat aaa aaa gct gca gag act tta atg gtc ctt gac    96
Pro Asn Thr Leu His Lys Lys Ala Ala Glu Thr Leu Met Val Leu Asp
            20                  25                  30 caa aat gaa cca                                                    108
Gln Asn Gln Pro
        35
```

<210> SEQ ID NO 47
<211> LENGTH: 90
<212> TYPE: DNA
<213> ORGANISM: Homo sapiens
<220> FEATURE:
<221> NAME/KEY: CDS
<222> LOCATION: (1)...(90)

<400> SEQUENCE: 47

```
ggg atc gga aaa cga aca aat gaa cat acg gca gat tgt aaa att aaa    48
Gly Ile Gly Lys Arg Thr Asn Glu His Thr Ala Asp Cys Lys Ile Lys
1               5                   10                  15 ccg aac acc ttg cat aaa aaa gct gca gag act tta atg gtc             90
Pro Asn Thr Leu His Lys Lys Ala Ala Glu Thr Leu Met Val
            20                  25                  30
```

<210> SEQ ID NO 48
<211> LENGTH: 75
<212> TYPE: DNA
<213> ORGANISM: Homo sapiens
<220> FEATURE:
<221> NAME/KEY: CDS
<222> LOCATION: (1)...(75)

<400> SEQUENCE: 48

```
ggg atc gga aaa cga aca aat gaa cat acg gca gat tgt aaa att aaa    48
Gly Ile Gly Lys Arg Thr Asn Glu His Thr Ala Asp Cys Lys Ile Lys
1               5                   10                  15 ccg aac acc ttg cat aaa aaa gct gca                                75
Pro Asn Thr Leu His Lys Lys Ala Ala
            20                  25
```

<210> SEQ ID NO 49
<211> LENGTH: 60
<212> TYPE: DNA
<213> ORGANISM: Homo sapiens
<220> FEATURE:
<221> NAME/KEY: CDS
<222> LOCATION: (1)...(60)

<400> SEQUENCE: 49

```
ggg atc gga aaa cga aca aat gaa cat acg gca gat tgt aaa att aaa    48
Gly Ile Gly Lys Arg Thr Asn Glu His Thr Ala Asp Cys Lys Ile Lys
1               5                   10                  15 ccg aac acc ttg                                                    60
Pro Asn Thr Leu
            20
```

<210> SEQ ID NO 50
<211> LENGTH: 45
<212> TYPE: DNA
<213> ORGANISM: Homo sapiens
<220> FEATURE:
<221> NAME/KEY: CDS
<222> LOCATION: (1)...(45)

<400> SEQUENCE: 50

```
ggg atc gga aaa cga aca aat gaa cat acg gca gat tgt aaa att      45
Gly Ile Gly Lys Arg Thr Asn Glu His Thr Ala Asp Cys Lys Ile
 1               5                  10                  15
```

<210> SEQ ID NO 51
<211> LENGTH: 42
<212> TYPE: DNA
<213> ORGANISM: Homo sapiens
<220> FEATURE:
<221> NAME/KEY: CDS
<222> LOCATION: (1)...(42)

<400> SEQUENCE: 51

```
ggg atc gga aaa cga aca aat gaa cat acg gca gat tgt aaa          42
Gly Ile Gly Lys Arg Thr Asn Glu His Thr Ala Asp Cys Lys
 1               5                  10
```

<210> SEQ ID NO 52
<211> LENGTH: 30
<212> TYPE: DNA
<213> ORGANISM: Homo sapiens
<220> FEATURE:
<221> NAME/KEY: CDS
<222> LOCATION: (1)...(30)

<400> SEQUENCE: 52

```
cga aca aat gaa cat acg gca gat tgt aaa                          30
Arg Thr Asn Glu His Thr Ala Asp Cys Lys
 1               5                  10
```

<210> SEQ ID NO 53
<211> LENGTH: 30
<212> TYPE: DNA
<213> ORGANISM: Artificial Sequence
<220> FEATURE:
<221> NAME/KEY: CDS
<222> LOCATION: (1)...(30)
<220> FEATURE:
<223> OTHER INFORMATION: Description of Artificial Sequence: Chemically
      synthesized nucleotide

<400> SEQUENCE: 53

```
cga aca aat gaa cat acg gca gaa tgt aaa                          30
Arg Thr Asn Glu His Thr Ala Glu Cys Lys
 1               5                  10
```

<210> SEQ ID NO 54
<211> LENGTH: 30
<212> TYPE: DNA
<213> ORGANISM: Artificial Sequence
<220> FEATURE:
<221> NAME/KEY: CDS
<222> LOCATION: (1)...(30)
<220> FEATURE:
<223> OTHER INFORMATION: Description of Artificial Sequence: Chemically
      synthesized nucleotide

<400> SEQUENCE: 54

```
cga aca caa gaa cat acg gca gaa tgt aaa   30
Arg Thr Gln Glu His Thr Ala Glu Cys Lys
 1               5                  10
```

<210> SEQ ID NO 55
<211> LENGTH: 30
<212> TYPE: DNA
<213> ORGANISM: Artificial Sequence
<220> FEATURE:
<221> NAME/KEY: CDS
<222> LOCATION: (1)...(30 )
<220> FEATURE:

<223> OTHER INFORMATION: Description of Artificial Sequence: Chemically
      synthesized nucleotide

<400> SEQUENCE: 55 cga aca caa gaa cat acg gca gat tgt aaa                                30
Arg Thr Gln Glu His Thr Ala Asp Cys Lys
  1               5                  10

<210> SEQ ID NO 56
<211> LENGTH: 30
<212> TYPE: DNA
<213> ORGANISM: Artificial Sequence
<220> FEATURE:
<221> NAME/KEY: CDS
<222> LOCATION: (1)...(30)
<220> FEATURE:
<223> OTHER INFORMATION: Description of Artificial Sequence: Chemically
      synthesized nucleotide

<400> SEQUENCE: 56 cga gca aat gaa cat acg gca gat tgt aaa                                30
Arg Ala Asn Glu His Thr Ala Asp Cys Lys
  1               5                  10

<210> SEQ ID NO 57
<211> LENGTH: 30
<212> TYPE: DNA
<213> ORGANISM: Artificial Sequence
<220> FEATURE:
<221> NAME/KEY: CDS
<222> LOCATION: (1)...(30)
<220> FEATURE:
<223> OTHER INFORMATION: Description of Artificial Sequence: Chemically
      synthesized nucleotide

<400> SEQUENCE: 57 cga aca gca gaa cat acg gca gat tgt aaa                                30
Arg Thr Ala Glu His Thr Ala Asp Cys Lys
  1               5                  10

<210> SEQ ID NO 58
<211> LENGTH: 30
<212> TYPE: DNA
<213> ORGANISM: Artificial Sequence
<220> FEATURE:
<221> NAME/KEY: CDS
<222> LOCATION: (1)...(30)
<220> FEATURE:
<223> OTHER INFORMATION: Description of Artificial Sequence: Chemically
      synthesized nucleotide

<400> SEQUENCE: 58 cga aca aat gaa cat gca gca gat tgt aaa                                30
Arg Thr Asn Glu His Ala Ala Asp Cys Lys
  1               5                  10

<210> SEQ ID NO 59
<211> LENGTH: 30
<212> TYPE: DNA
<213> ORGANISM: Artificial Sequence
<220> FEATURE:
<221> NAME/KEY: CDS
<222> LOCATION: (1)...(30)
<220> FEATURE:
<223> OTHER INFORMATION: Description of Artificial Sequence: Chemically
      synthesized nucleotide

<400> SEQUENCE: 59

-continued

```
cga aca aat gaa cat aca ggg gat tgt aaa                              30
Arg Thr Asn Glu His Thr Gly Asp Cys Lys
 1               5                  10
```

<210> SEQ ID NO 60
<211> LENGTH: 30
<212> TYPE: DNA
<213> ORGANISM: Artificial Sequence
<220> FEATURE:
<221> NAME/KEY: CDS
<222> LOCATION: (1)...(30)
<220> FEATURE:
<223> OTHER INFORMATION: Description of Artificial Sequence: Chemically
      synthesized nucleotide

<400> SEQUENCE: 60

```
cga aca aat gaa cat aca gca gat tat aaa                              30
Arg Thr Asn Glu His Thr Ala Asp Tyr Lys
 1               5                  10
```

<210> SEQ ID NO 61
<211> LENGTH: 30
<212> TYPE: DNA
<213> ORGANISM: Artificial Sequence
<220> FEATURE:
<221> NAME/KEY: CDS
<222> LOCATION: (1)...(30)
<220> FEATURE:
<223> OTHER INFORMATION: Description of Artificial Sequence: Chemically
      synthesized nucleotide

<400> SEQUENCE: 61

```
cga aca caa gaa cat aca gca gaa gca aaa                              30
Arg Thr Gln Glu His Thr Ala Glu Ala Lys
 1               5                  10
```

<210> SEQ ID NO 62
<211> LENGTH: 30
<212> TYPE: DNA
<213> ORGANISM: Artificial Sequence
<220> FEATURE:
<221> NAME/KEY: CDS
<222> LOCATION: (1)...(30)
<220> FEATURE:
<223> OTHER INFORMATION: Description of Artificial Sequence: Chemically
      synthesized nucleotide

<400> SEQUENCE: 62

```
cga aca caa gaa cat aca gca gaa tat aaa                              30
Arg Thr Gln Glu His Thr Ala Glu Tyr Lys
 1               5                  10
```

<210> SEQ ID NO 63
<211> LENGTH: 30
<212> TYPE: DNA
<213> ORGANISM: Artificial Sequence
<220> FEATURE:
<221> NAME/KEY: CDS
<222> LOCATION: (1)...(30)
<220> FEATURE:
<223> OTHER INFORMATION: Description of Artificial Sequence: Chemically
      synthesized nucleotide

<400> SEQUENCE: 63

```
cga aca caa gaa cat aca gca gaa tct aaa                              30
Arg Thr Gln Glu His Thr Ala Glu Ser Lys
 1               5                  10
```